United States Patent [19]

Liebeskind et al.

[11] Patent Number: 5,959,014

[45] Date of Patent: *Sep. 28, 1999

[54] WATER-STABILIZED ORGANOSILANE COMPOUNDS AND METHODS FOR USING THE SAME

[75] Inventors: Lanny S. Liebeskind, Atlanta; Gary D. Allred, Norcross, both of Ga.

[73] Assignee: Emory University, Atlanta, Ga.

[*] Notice: This patent issued on a continued prosecution application filed under 37 CFR 1.53(d), and is subject to the twenty year patent term provisions of 35 U.S.C. 154(a)(2).

[21] Appl. No.: 08/646,156

[22] Filed: May 7, 1996

[51] Int. Cl.⁶ .................................................. C08K 3/20
[52] U.S. Cl. .......................... 524/389; 524/386; 524/387; 524/540; 524/541; 524/506; 524/588; 524/474; 524/480; 524/509; 424/401; 424/404
[58] Field of Search ...................................... 524/386, 540, 524/541, 506, 588, 474, 480, 509, 387, 389; 528/28; 424/401, 404

[56] References Cited

U.S. PATENT DOCUMENTS

| | | | |
|---|---|---|---|
| 3,403,721 | 10/1968 | Robins et al. | 164/43 |
| 3,794,736 | 2/1974 | Abbott et al. | 424/78 |
| 3,817,739 | 6/1974 | Abbott et al. | 71/67 |
| 3,865,728 | 2/1975 | Abbott et al. | 210/169 |
| 4,035,332 | 7/1977 | Gomyo et al. | 260/33.2 SB |
| 4,110,263 | 8/1978 | Lindemann et al. | 252/545 |
| 4,243,767 | 1/1981 | Kaufman et al. | 525/102 |
| 4,284,548 | 8/1981 | Kaufman et al. | 260/38 |
| 4,413,086 | 11/1983 | Chang et al. | 524/386 |
| 4,446,292 | 5/1984 | Chang et al. | 528/29 |
| 4,465,849 | 8/1984 | Tarae et al. | 556/450 |
| 4,467,081 | 8/1984 | Chang et al. | 528/26 |
| 4,501,872 | 2/1985 | Chang et al. | 528/18 |
| 4,514,342 | 4/1985 | Billington et al. | 260/952 |
| 4,555,545 | 11/1985 | Kimura et al. | 524/858 |
| 4,561,435 | 12/1985 | McKnight et al. | 128/156 |
| 4,613,451 | 9/1986 | Chang et al. | 252/182 |
| 4,615,882 | 10/1986 | Stockel | 424/80 |
| 4,622,369 | 11/1986 | Chang et al. | 525/440 |
| 4,623,697 | 11/1986 | Chang et al. | 525/61 |
| 4,631,273 | 12/1986 | Blehm et al. | 514/29 |
| 4,631,297 | 12/1986 | Battice et al. | 521/78 |
| 4,648,904 | 3/1987 | DePasquale et al. | 106/2 |
| 4,657,941 | 4/1987 | Blackwell et al. | 522/14 |
| 4,736,467 | 4/1988 | Schwarze et al. | 2/114 |
| 4,772,593 | 9/1988 | Whalen et al. | 514/63 |
| 4,822,667 | 4/1989 | Goad et al. | 428/265 |
| 4,842,766 | 6/1989 | Blehm et al. | 252/309 |
| 4,919,998 | 4/1990 | Goad et al. | 428/265 |
| 4,939,289 | 7/1990 | Oxenrider et al. | 560/87 |
| 4,990,338 | 2/1991 | Blank et al. | 424/443 |
| 5,024,851 | 6/1991 | Goad et al. | 427/2 |
| 5,027,438 | 7/1991 | Schwarze et al. | 2/114 |
| 5,035,892 | 7/1991 | Blank et al. | 424/443 |
| 5,064,613 | 11/1991 | Higgs et al. | 422/16 |
| 5,070,215 | 12/1991 | Bambury et al. | 556/418 |
| 5,073,298 | 12/1991 | Gentle et al. | 252/358 |
| 5,135,811 | 8/1992 | White et al. | 428/395 |
| 5,244,718 | 9/1993 | Taylor et al. | 428/229 |
| 5,411,585 | 5/1995 | Avery et al. | 106/287.1 |

OTHER PUBLICATIONS

S. F. Hayes and W. C. White, How Antimicrobial Treatment Can Improve Nonwovens, Reprinted from the American Dyestuff Reporter (1984).

R. L. Gettings and B. L. Triplett, A New, Durable Antimicrobial Finish for Textiles, Reprinted from the 1978 Book of Paper, pp. 259–261, 1978 American Association of Textile Chemists and Colorists National Technical Conference.

P. A. Walters, E. A. Abbott and A. J. Isquith, Algicidal Activity of a Surface–Bonded Organosilicon Quaternary Ammonium Chloride, Applied Microbiology, 25: 253–256 (1973).

J. B. McGee, J. R. Malek and W. C. White, New Antimicrobial Treatment for Carpet Applications, Reprinted from the Jun. 1983 issue of American Dyestuff Reporter by Dow Corning Corp.

A. J. Isquith, E. A. Abbott and P. A. Walter, Surface–Bonded Antimicrobial Activity of an Organosilicon Quaternary Ammonium Chloride, Applied Microbiolody 24:859–863 (1972).

W. D. Hanrahan and A. S. Patil, Fighting Bacteria From Within, Textile Technology International, pp. 173–175 (1996).

M. Gruender, New Acetate Works Against Bacteria, FW:Fiber Technology (Jan. 1996).

*Primary Examiner*—Jeffrey Stucker
*Attorney, Agent, or Firm*—Needle & Rosenberg, P.C.

[57] ABSTRACT

The product of reacting an organosilane optionally having a nonhydrolizable organic group, but having one or more hydrolyzable groups, with a polyol containing at least three hydroxy groups, where any two of the hydroxy groups are separated by at least three intervening atoms. Water-stabilized organosilane compounds. A water stable composition made from the product or compound and water. A method of treating a substrate by contacting the substrate with the product, compound, or composition for a period of time sufficient for treatment of the substrate. A treated substrate having adhered thereto the product, compound, or composition.

44 Claims, No Drawings

WATER-STABILIZED ORGANOSILANE COMPOUNDS AND METHODS FOR USING THE SAME

BACKGROUND OF THE INVENTION

1. Field of the Invention

The invention relates to organosilane compounds, products and methods for their use. In particular, this invention provides water-stable organosilane compounds, products, and compositions for treating various substrates, articles treated with the compounds, products and compositions, and methods of treatment using the compounds, products and compositions.

2. Background

Organosilanes of the general formula $R_nSiX_{4-n}$, where n is an integer of from 0 to 3, but more generally from 0 to 2 (where when n is 3 the organosilanes may only dimerize); R is a nonhydrolizable organic group, such as, but not limited to, alkyl, aromatic, organofunctional, or a combination thereof, and X is alkoxy, such as methoxy or ethoxy, are prone to self-condensation rendering such organosilanes unstable in water over commercially relevant periods of time. Additionally, X can be a halogen, such as Cl, Br, or I, and is similarly liberated as HCl, HBr, or HI. For such organosilanes, the X moiety reacts with various hydroxyl containing molecules in aqueous media to liberate methanol, ethanol, HCl, HBr, HI, $H_2O$, acetic acid, or an unsubstituted or substituted carboxylic acid to form the hydroxylated, but condensation-prone compound.

For organosilanes $R_nSiX_{4-n}$, where n is an integer from 0 to 2, hydrolysis of the first two X groups with water produces a species bearing $-Si(OH)_2-$ units which can self-condense through the hydroxyl moieties to linear and/or cyclic oligomers possessing the partial structure HO—Si—(O—Si)$_{mm}$—O—Si—O—Si—O—Si—OH, where mm is an integer such that an oligomer is formed. For those cases, $RSiX_3$, hydrolysis of the third X group generates a silanetriol $(RSi(OH)_3)$ which produces insoluble organosilicon polymers through linear and/or cyclic self-condensation of the Si(OH) units. This water induced self-condensation generally precludes storage of most organosilanes $R_nSiX_{4-n}$, where n ranges from 0 to 2, inclusive, in water. Except for some organosilanes which can be stable in very dilute solutions at specific pH ranges, the use of water solutions of most organosilanes require the use of freshly prepared solutions.

One commercially relevant example of an organosilane suffering from such undesirable self-condensation is the antimicrobial Dow Corning 5700 (Dow Corning Corporation, Midland, Mich.). The literature describes the active ingredient of Dow Corning 5700 as 3-(trimethoxysilyl)propyl-dimethyloctadecyl ammonium chloride. However, in aqueous media, it is believed that the correct active ingredient is more likely 3-(trihydroxysilyl) propyl-dimethyloctadecyl ammonium chloride. Nonetheless, 3-(trimethoxysilyl)propyl-dimethyloctadecyl ammonium chloride is a water activated antimicrobial integrated system which is capable of binding to a wide variety of natural and synthetic substrates, including fibers and fabrics, to produce a durable surface or fabric coating. 3-(Trimethoxysilyl)propyl-dimethyloctadecyl ammonium chloride is prepared by quaternization of dimethyloctadecylamine with 3-chloropropyl trimethoxysilane. See Scheme 1.

Scheme 1

$CH_3(CH_2)_{16}CH_2N(CH_3)_2 + ClCH_2CH_2CH_2Si(OCH_3)_3$

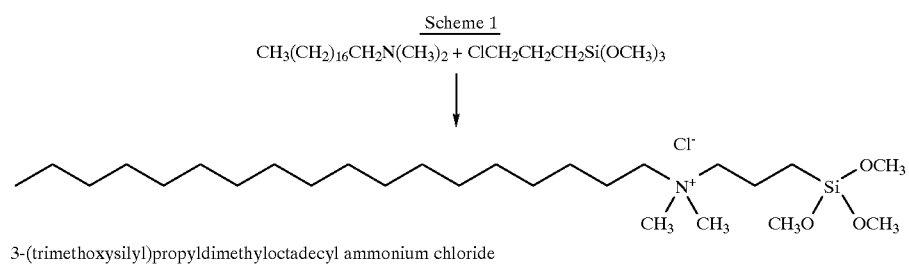

3-(trimethoxysilyl)propyldimethyloctadecyl ammonium chloride

The $C_{18}$ hydrocarbon chain quaternary ammonium portion of the molecule in Scheme 1 possesses long-acting antimicrobial properties and provides initial association with the surface of the substrate through ionic bonds and/or electrostatic interaction. Moreover, in the presence of water and as generally described above, the propyl trimethoxysilane portion of the molecule converts into a propyl trihydroxysilyl moiety and polymerizes through Si—O bonds to hydroxylated surfaces of the substrate and through intermolecular O—Si bonds. Therefore, the traditional method of use of 3-(trimethoxysilyl)propyl-dimethyloctadecyl ammonium chloride is to add a dilute solution of 3-(trimethoxysilyl)propyl-dimethyloctadecyl ammonium chloride in methanol to water. This addition rapidly converts the $-Si(OCH_3)_3$ portion of the molecule into a reactive $-Si(OH)_3$ group thereby activating the molecule. The activated 3-(trihydroxysilyl)propyl-dimethyloctadecyl ammonium chloride system must then be used within a short period of time, such as a few hours to at most about 12 hours, to treat a surface or fabric to produce a permanent surface coating. Scheme 2 shows a two-stage process which is believed to represent the coating reaction.

Scheme 2

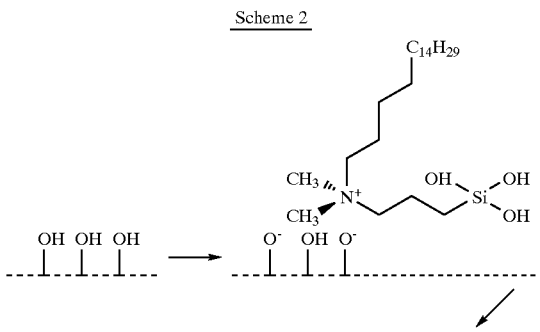

-continued

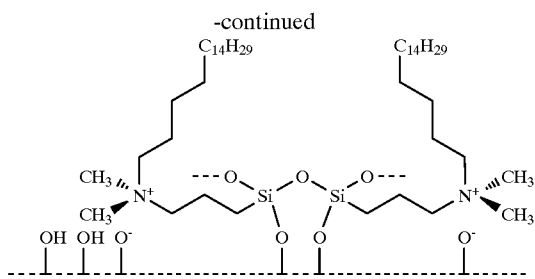

First, as shown in Scheme 2, initial association of the 3-(trihydroxysilyl)propyl-dimethyloctadecyl ammonium chloride with the surface occurs either through ionic bonding between a negatively charged surface O⁻ and the positively charged ammonium ion (if the surface is hydroxylated with acidic OH groups), or through covalent bonds between a surface OH and a —Si—OH group (if the surface possesses non-acidic OH groups), or, for non-hydroxylated surfaces, through electrostatic attraction between the negative charge that exists on most surfaces and the positively charged ammonium ion. After association of water-activated 3-(trihydroxysilyl)propyl-dimethyloctadecyl ammonium chloride with the surface, it is thought that permanent bonding to the surface occurs through a combination of additional surface OH to —Si—OH bonds with hydroxylated surfaces, and more importantly through intermolecular siloxane polymerization (—Si—O—Si— bonds). It should be noted that it is not always the case that the trihydroxysilyl species is the moiety that binds to the substrate surface. The trimethoxysilyl species may also undergo association and/or binding to the surface and undergo polymerization with a loss of methanol. Nonetheless, once the siloxane is polymerized, the treated surface becomes permanently coated with a covalently bound octadecylammonium ion, providing a durable, long-acting antimicrobial coating that is able to destroy microbes that come into contact with the surface.

Unfortunately, as noted above, organosilanes in water, such as the activated mixture of 3-(trihydroxysilyl)propyl-dimethyloctadecyl ammonium chloride and water, are generally unstable and prone to self-condensation. For instance, the mixture of 3-(trihydroxysilyl)propyl-dimethyloctadecyl ammonium chloride and water begins to lose effectiveness in as little as four to eight hours. Gel formation in this and similar silane formulations in water begins to occur in even shorter times. The limitations of such organosilanes in aqueous media are further described in U.S. Pat. No. 5,411,585, the contents of which are hereby incorporated by this reference. Moreover, such products are notorious for agitation difficulty during the addition of the silane to water.

The use of quaternary ammonium silicon compounds as antimicrobial agents in accordance with the prior art is well known and taught in a wide variety of U.S. Pat. Nos. e.g., 3,560,385; 3,794,736; 3,814,739, the contents of which are hereby incorporated by this reference. It is also taught that these compounds possess certain antimicrobial properties which make them valuable and very useful for a variety of surfaces, substrates, instruments and applications (see, e.g., U.S. Pat. Nos. 3,730,701; 3,794,736; 3,860,709; 4,282,366; 4,504,541; 4,615,937; 4,692,374; 4,408,996; and 4,414,268, the contents of which are hereby incorporated by this reference). While these quaternary ammonium silicon compounds have been employed to sterilize or disinfect many surfaces, their employment is still limited because of their toxicity often as a result of the solvent system used to deliver the compound, the necessity for a solvent solution (for instance, Dow Corning antimicrobial agents contain 50% methanol), short term stability (stability of aqueous silane solutions varies from hours to several weeks only) and poor water solubility. For instance, while 3-(trimethoxysilyl) propyl-dimethyloctadecyl ammonium chloride does not suffer from water insolubility, it is unstable in water and also, because it is shipped in 50% methanol, it is overly toxic. Many other antimicrobial organosilanes, especially quaternary ammonium silicon compounds, also suffer from problems associated with physical health hazards, e.g., precautions must be taken to avoid contact with both skin and eyes, accidental spills to the surrounding area, flammability, and the added manufacturing steps needed in order to incorporate the such antimicrobial agents into other articles and surfaces, resulting in much higher manufacturing cost.

Therefore, there exists a need for extended shelf-life, water-stable organosilane compounds, products and compositions whereby, upon application, the active portion of the organosilane is operative for the selected application. Moreover, there exists a need for water-stable, organosilane compounds, products and compositions which are essentially non-toxic, non-flammable, uniformly dispersable, and simple and economical to use.

SUMMARY OF THE INVENTION

The present invention fulfills these needs by providing water-stable organosilane compounds, products (i.e., the compounds or compositions formed from performing a specified reaction) and compositions, methods for their use, and articles prepared using the compounds, products, and compositions. The compounds, products, and compositions of the present invention are non-toxic, non-flammable, simple, economical and are operable over a wide variety of pH ranges.

In particular, the present invention provides the product formed from reacting an organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms.

In an alternate embodiment, the present invention provides a compound having the formula $(R)_nSi(X)_{4-n-y}(R_{41})_y$ wherein n is an integer of from 0 to 3, preferably 0 to 2; y is an integer of from 1 to 4; each R is, independently, a nonhydrolizable organic group; each X is, independently, a hydrolyzable group; and each $R_{41}$, is, independently, a polyol containing at least three hydroxy groups, wherein any two of the at least three hydroxy groups are separated by at least three intervening atoms and wherein the polyol is bonded to the Si by removal of the hydrogen from one of the at least three hydroxy groups such that the oxygen of the one of the at least three hydroxy groups is bonded to Si.

In a further embodiment, the present invention provides a compound having the formula VIII, IX, X or XI:

$$\{[R_{22}(CH_2)_t]_2C(R_{23})(R_{24})\}_m(OH)_{3-m}SiR_{25}N^+(R_{26})(R_{27})(R_{28})U^- \quad (VIII)$$

$$\{[R_{22}(CH_2)_t]_2C(R_{23})(R_{24})\}_m(OH)_{3-m}SiR_{25}N(R_{26})(R_{27}) \quad (IX)$$

$$\{[R_{22}(CH_2)_t]_2C(R_{23})(R_{24})\}_u(OH)_{3-u}SiR_{25}R_{38} \quad (X)$$

$$\{[R_{22}(CH_2)_t]_2C(R_{23})(R_{24})\}_v(OH)_{2-v}Si(R_{39})(R_{40}) \quad (XI)$$

wherein m is an integer of from 1 to 3; i is an integer of from 1 to 2; u is an integer of from 0 to 3; v is an integer of from 0 to 2; each $R_{22}$ is, independently, H or $OR_{33}$ where $R_{33}$ is, independently, $[-CH_2C(CH_2OH)_2CH_2O]_f$—H where f is an integer of from 0 to 5; $R_{33}$ is H, halogen, $NH_2(CH_2)_2$ $NHR_{25}$, $NH_2R_{25}$, $C_3H_5O_2R_{25}$, $C_4H_5O_2R_{25}$, $NaO(CH_3O)P(O)R_{25}$, or $ClCH_2C_6H_4R_{25}$; $R_{39}$ and $R_{40}$ are, independently, halogen, H, alkyl of from 1 to about 8 carbon atoms, isobutyl, phenyl, or n-octyl; $R_{23}$ and $R_{24}$ are, independently, halogen, H, $CH_2OH$, $N(CH_2CH_2OH)_2CH_3{}^+Q^-$, $NH_2$, $NO_2$, $N(H)(CH_2)_3OSO_3H$, $N^+(CH_3)_2(CH_2)_3SO_3{}^+$, $N(CH_3)_3{}^+Q^-$, $(CH_2)OPO_3H_2$, $(CH_2)PO_3H_2$, $N(H)R_{34}(CF_2)_eCF_3$ where e is an integer of from 1 to about 22 and $R_{34}$ is CO or $SO_2$, $(W)_pZO$ where Z is H, alkyl, aryl, or heteroaryl, $(W)_pZS(O)_r$ where Z is H, Na, a suitable mono- or di-valent cation, alkyl, aryl, or heteroaryl and r is an integer from 0 to 2, $(W)_pZ_1Z_2N$ where $Z_1$ and $Z_2$ are, independently, H, alkyl, aryl, or heteroaryl, $(W)_pZ_3Z_4Z_5N^+Q$ where $Z_3$, $Z_4$, and $Z_5$ are, independently, H, alkyl, aryl, or heteroaryl, or $(W)_pZ_6PO_3$ where $Z_6$ is H, Na, a suitable mono- or di-valent cation, alkyl, aryl, or heteroaryl; where p is an integer from 0 to 1; W is alkyl, polyether, aryl or heteroaryl, and $Q^-$ is a suitable anionic moiety to form the salt of the compound of formula VIII, IX, X, or XI; $R_{25}$, is benzyl, vinyl, or alkyl of from 1 to about 3 carbon atoms; $R_{26}$ and $R_{27}$ are, independently, lower alkyl alcohol, lower alkoxy of from 1 to 4 carbon atoms, alkyl of from 1 to about 22 carbon atoms, preferably 1 to about 10 carbon atoms; or $R_{26}$ and $R_{27}$ can, together, form a morpholine or cyclic or heterocyclic, unsaturated or saturated, five to seven-membered ring of the formula XII:

$$—R_{26}—(R_{29})_h—R_{27}— \quad (XII)$$

where h is an integer from 0 to 2 and $R_{29}$, where the ring is saturated, is $CH_2$, O, S, NH, $NH_2{}^+$, $NCH_2CH_2NH_2$, $NCH_2CH_2NH_3{}^+$, $NCH_2CH_2N(R_8)(R_9)$, $CH_2CH_2N^+(R_{30})(R_{31})(R_{32})$, N(alkyl), N(aryl), N(benzyl) where $R_{30}$, $R_{31}$, and $R_{32}$ are, independently, benzyl, polyether, lower alkyl alcohol, lower alkoxy of from 1 to 4 carbon atoms, alkyl of from 1 to about 22 carbon atoms, preferably 1 to about 10 carbon atoms, and $R_{29}$, where the ring is unsaturated is, CH, N, $N^+H$, $N^+(alkyl)$, $N^+(aryl)$, $N^+(benzyl)$, $N—CH_2—N$, $N^+H—CH_2—N$, $N^+(alkyl)—CH_2—N$, $N^+(aryl)—CH_2{}^+N$, or $N^+(benzyl)—CH_2—N$; wherein the ring is unsubstituted or substituted with alkyl of from 1 to 22 carbon atoms, ester, aldehyde, carboxylate, amide, thionamide, nitro, amine, or halide; $R_{28}$ is lower alkyl alcohol, $CH_2C_6H_5$, polyether, alkyl, alkoxy, perfluoroalkyl, perfluoroalkylsulfonate, or perfluoroalkylcarboxylate wherein the alkyl, alkoxy, perfluoroalkyl, perfluoroalkylsulfonate, or perfluoroalkylcarboxylate is of from 1 to about 22 carbon atoms; and $U^-$ is a suitable anionic moiety to form the salt of the compound of formula XII.

In yet another embodiment, the present invention provides a compound having the formula XIII:

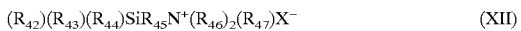

$$(R_{42})(R_{43})(R_{44})SiR_{45}N^+(R_{46})_2(R_{47})X^- \quad (XII)$$

wherein X is halogen; $R_{44}$ is lower alkyl of from 1 to 3 carbon atoms; $R_{46}$ is lower alkyl of from 1 to 3 carbon atoms; $R_{47}$ is alkyl of from 1 to 22 carbon atoms; $R_{42}$, $R_{43}$ and $R_{44}$ are, independently, OH, $CH_2OH$, or $(—OCH_2)C(Z)(R_6)(R_7)$, wherein each Z is, independently, $—CH_2OH$, $—CH_3$, $—NH_2$, $—NO_2$, $—(CH_2)OPO_3H_2$, $—(CH_2)PO_3H_2$, $—N^+(CH_3)_3Cl^-$, $N(H)(CH_2)_3OSO_3H$, or $N^+(CH_3)_2(CH_2)_3SO_3^-$, provided that at least one of $R_{42}$ $R_{43}$, and $R^{44}$ is not OH or $CH_2OH$.

In yet a further embodiment, the present invention provides a water stable composition, comprising the product or compound of the invention and water.

In a further embodiment, the present invention provides a composition for treating a substrate, comprising a carrier and an effective amount of the product or compound of the invention.

In yet another embodiment, the present invention provides a compound having the formula $(R)_nSi(X)_{4-n-y}$, $(R_{41})_y$ wherein n is an integer of from 0 to 3, preferably 0 to 2; y is an integer of from 1 to 4; each R is, independently, a nonhydrolizable organic group; each X is, independently, a hydrolyzable group; and each $R_4$, is, independently, a poly(tetrahydrofuran), a poly(vinyl)alcohol, hydroxyethyl cellulose, starch, or a cellulosic derivative, containing at least three hydroxy groups, wherein any two of the at least three hydroxy groups are separated by at least three intervening atoms and wherein the $R_{41}$ bonded to the Si by removal of the hydrogen from one of the at least three hydroxy groups such that the oxygen of the one of the at least three hydroxy groups is bonded to Si.

In yet another embodiment, the present invention provides a product formed from reacting an organosilane of the formula II, III, IV, or V:

$$(R_1)_3SiR_2N^+(R_3)(R_4)(R_5)Y^+ \quad (II)$$

$$(R_1)_3SiR_2N(R_3)(R_4) \quad (III)$$

$$(R_1)_3SiR_2R_{35} \quad (IV)$$

$$(R_1)_2Si(R_{36})(R_{37}) \quad (V)$$

wherein each $R_1$ of the three is, independently, halogen or $R_6O$, where $R_6$ is H, alkyl of from 1 to about 6 carbon atoms, acetyl, acetoxy or acyl; $R_{35}$ is H, halogen, $NH_2(CH_2)_2NHR_2$, $NH_2R_2$, $C_3H_5O_2R_2$, $C_4H_5O_2R_2$, $NaO(CH_3O)P(O)R_2$, or $ClCH_2C_6H_4R_2$; $R_{36}$ and $R_{37}$ are, independently, halogen, H, alkyl of from 1 to about 8 carbon atoms, isobutyl, phenyl, or n-octyl; $R_2$ is benzyl, vinyl or alkyl of from 1 to about 3 carbon atoms; $R_3$ and $R_4$ are, independently, lower alkyl alcohol of from 1 to 4 carbon atoms, lower alkoxy of from 1 to 4 carbon atoms, or alkyl of from 1 to about 22 carbon atoms, preferably 1 to about 10 carbon atoms, preferably 1 to about 10 carbon atoms, or $R_3$ and $R_4$ can, together, form a morpholine or cyclic or heterocyclic, unsaturated or saturated, five to seven-membered ring of the formula VI:

$$—R_3—(R_7)_k—R_4— \quad (VI)$$

where k is an integer from 0 to 2, $R_7$, where the ring is saturated, is $CH_2$, O, S, NH, $NH_2{}^+$, $NCH_2CH_2NH_2$, $NCH_2CH_2NH_3{}^+$, $NCH_2CH_2N(R_8)(R_9)$, $NCH_2CH_2N^+(R_8)(R_{10})$, N(alkyl), N(aryl), N(benzyl), where each $R_8$, $R_9$, and $R_{10}$, is, independently benzyl, polyether, lower alkyl alcohol of from 1 to 4 carbon atoms, lower alkoxy of from 1 to 4 carbon atoms, or alkyl of from 1 to about 22 carbon atoms, preferably 1 to about 10 carbon atoms, and $R_7$, where the ring is unsaturated is, CH, N, $N^+H$, $N^+(alkyl)$, $N^+(aryl)$, $N^+(benzyl)$, $N—CH_2—N$, $N^+H—CH_2—N$, $N^+(alkyl)—CH_2—N$, $N^+(aryl)—CH_2—N$, or $N^+(benzyl)—CH_2—N$; wherein the ring is unsubstituted or substituted with alkyl of from 1 to 22 carbon atoms, ester, aldehyde, carboxylate, amide, thionamide, nitro, amine, or halide, $R_5$ is lower alkyl alcohol, $CH_2C_6H_5$, polyether, alkyl, alkoxy, perfluoroalkyl, perfluoroalkylsulfonate, or perfluoroalkylcarboxylate wherein the alkyl, alkoxy, perfluoroalkyl, perfluoroalkylsulfonate, or perfluoroalkylcarboxylate is of from 1 to about 22 carbon atoms; and Y⁻ is a suitable anionic moiety to form the salt of the compound of formula II, III, IV or V; with a poly(tetrahydrofuran), a poly(vinyl) alcohol, hydroxyethyl cellulose, starch, a cellulosic derivative, or a mixture thereof.

In a further embodiment, the present invention provides a product as described above, wherein the polyol is of the formula XIV:

$$(HOCH_2)_{aa}C[CH_2OP(R_{60})(R_{61})]_{4-aa} \qquad (XIV)$$

or is aryl substituted with from 2 to 6 moieties of —(OCH$_2$)C(CH$_2$OH)$_3$; wherein aa is an integer of from 0 to 4; each $R_{60}$ is, independently, O$_2$ or OH; and each $R_{61}$, is, independently, H, a mono- or di-valent cation, or OR$_{62}$ where $R_{62}$ is alkyl of from 1 to 22 carbon atoms, lower alkyl alcohol of from 1 to 4 carbon atoms, or alkoxy of from 1 to 4 carbon atoms.

In yet another embodiment, the present invention provides a method of treating a substrate, comprising contacting the substrate with a sufficient amount of the product, compound or composition of the invention for a period of time sufficient for treatment of the substrate.

In a further embodiment, the present invention provides a treated substrate having adhered thereto the product, compound or composition of the invention.

In addition, the present invention provides a method of dyeing and treating a substrate, comprising contacting the substrate with an aqueous composition comprising an aqueous soluble dye suitable for dyeing a substrate and the product formed from reacting an organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to dye and treat the substrate.

In a further embodiment, the present invention provides a method of antimicrobially treating a food article, comprising contacting the food article with an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to antimicrobially treat the food article.

In yet another embodiment, the present invention provides a method of antimicrobially coating a fluid container used for containing a human or animal consumable product, comprising contacting the container with an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to antimicrobially coat the container.

In yet another embodiment, the present invention provides a method of antimicrobially coating a latex medical article for use in a human or animal medical procedure, comprising contacting the article with an effective amount of the product formed from reacting an antimicrobial organosilane of the formula $R_nSiX_{4-n}$ where n is an integer of from 0 to 3, preferably 0 to 2; each R is, independently, a nonhydrolizable organic group, and each X is, independently, a hydrolyzable group, with a polyol containing at least three hydroxy groups, wherein any two of the at least three hydroxy groups are separated by at least three intervening atoms, for a period of time sufficient to antimicrobially coat the article.

A further embodiment of the present invention provides a method of antimicrobially treating a substrate selected the group consisting of a concrete pipe, a tooth brush, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from reacting an antimicrobial organosilane of the formula $R_nSiX_{4-n}$ where n is an integer of from 0 to 3, preferably 0 to 2, each R is, independently, a nonhydrolizable organic group, and each X is, independently, a hydrolyzable group, with a polyol containing at least three hydroxy groups, wherein any two of the at least three hydroxy groups are separated by at least three intervening atoms, for a period of time sufficient to antimicrobially treat the substrate.

In addition, the present invention also provides a method of antimicrobially enhancing a product of grout, rubbing alcohol, a flower preservative, or a waterproofing solution, comprising admixing with the product an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to antimicrobially enhance the product.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

The present invention may be understood more readily by reference to the following detailed, description of preferred embodiments of the invention.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

The term "alkyl" as used herein refers to a branched or unbranched saturated hydrocarbon group of 1 to 24 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl and the like. Preferred alkyl groups herein contain from 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms. "Lower alkyl alcohol" refers to lower alkyl having attached thereto one or more hydroxy moieties, such as, but not limited to, $-CH_2CH_2OH$, $CH_2CH(OH)CH_3$, $CH_2OH$, $CH_2CH_2CH_2OH$, $CH_2CH_2CH(OH)CH_3$, $CH_2CH_2CH(OH)CH_2OH$, or $CH_2CH(OH)CH(OH)CH_3$.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms. "Polyether" refers to a compound or moiety possessing multiple ether linkages, such as, but not limited to, polyethylene glycols or polypropylene glycols. "Polyalkylethers" refers to alkyls interconnected by or otherwise possessing multiple ether linkages.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound, product, or composition as provided herein is meant a sufficient amount of the compound, product or composition to provide the desired result. As will be pointed out below, the exact amount required will vary from substrate to substrate, depending on the particular compound, product or composition used, its mode of administration, and the like. Thus, it is not always possible to specify an exact "effective amount." However, an appropriate effective amount may be determined by one of ordinary skill in the art using only routine experimentation.

The term "aryl" as used herein refers to a compound or moiety whose molecules have a ring or multiple ring structure characteristic of benzene, naphthalene, phenanthrene, anthracene, etc., i.e., either the six-carbon ring of benzene or the condensed six-carbon rings of the other aromatic derivatives, including, but not limited to phenyl, benzyl, naphthyl, benzylidine, xylil, styrene, styryl, phenethyl, phenylene, benzenetriyl, etc. As used herein, the term "aromatic" refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. Aromatics include the cyclic compounds based upon a benzene functionality, as specified for "aryl" above. Moreover, the term "cyclic" is used to refer to all aliphatic or aromatic hydrocarbons having one or more closed rings, whether unsaturated or saturated. Preferably, cyclic compounds possess rings of from 5 to 7 carbon atoms, preferably 6 carbon atoms. Such rings fall into three classes: alicyclic, aromatic ("arene"), and heterocyclic. Moreover, when used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds, i.e., where all available valence bonds of an atom, especially carbon, are attached to other atoms.

The term "heteroaryl" refers to an aryl where one or more of the carbon atoms of a ring have been substituted with a heteroatom, including, but not limited to, O, N, or S. Similarly, the term "heterocyclic" refers to a cyclic compound or moiety where one or more of the carbon atoms of the ring has been substituted with a heteroatom, including, but not limited to, O, N, or S.

As used herein, especially in reference to alkyl and alkoxy, the term "lower" refers to a moiety having from 1 to 6 carbon atoms, preferably 1 to 4 carbon atoms.

As used herein, the term "suitable" is used to refer a moiety which is compatible with the compounds, products, or compositions as provided herein for the stated purpose. Suitability for the stated purpose may be determined by one of ordinary skill in the art using only routine experimentation.

As used herein, "substituted" is used to refer, generally, to a carbon or suitable heteroatom having a hydrogen or other atom removed and replaced with a further moiety. In one embodiment, halogen, hydroxy, and nitrogen based substitutions of hydrocarbon hydrogens are contemplated as within the scope of the present invention for the claimed structures. Moreover, it is intended that "substituted" refer to substitutions which do not change the basic and novel utility of the underlying compounds, products or compositions of the present invention. "Unsubstituted" refers to a structure wherein the reference atom does not have any further moieties attached thereto or substituted therefor.

As used herein, "branched" is used to refer, generally, to a moiety having a carbon chain backbone, e.g., alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)_2CH_3$, and $CH_2CH_2C(CH_3)_3$ would all be considered branched moieties. Moreover, it is intended that "branched" variations of the moieties herein described refer to variations which do not change the basic and novel utility of the underlying compounds, products or compositions of the present invention. "Unbranched" refers to a structure wherein the carbon chain does not have any branches thereon, i.e., where the carbon chain extends in a direct line.

As used herein, the term "acyl" refers to organic acid derived moieties of the formula RCOX where R is an organic molecule and X, instead of being hydroxy, is replaced with another substituent, preferably, a suitable anion, such as a halogen including, but not limited to, F, Cl, Br or I.

As used herein, the term "perfluoro" or "perfluoro- analog" refers to a hydrocarbon where the hydrogen atoms attached to carbons have been replaced with F atoms. Preferably, but not necessarily, in perfluoro- analogs, most if not all of the H atoms are replaced with F atoms. A "fluoro-" analog is contemplated to indicate a hydrocarbon where at least one hydrogen atom attached to a carbon is replaced with an F atom.

As used herein, "substrate" refers to any article, product, or other surface that can be treated with the inventive compounds, preferably as enumerated hereinbelow under the heading Uses, as described in the Examples hereto, and as specified in the relevant claims appended hereto. Suitable substrates are generally characterized in preferably having a negatively charged surface of oxygen atoms, or any surface capable of electrostatically, ionically or covalently adhering or binding to the compounds, products, or compositions of the present invention. Preferably the adhering or binding occurs at the silicon atom of the organosilane portion of the compounds, products, or compositions of the present invention, but such binding is not a requirement. Therefore, as used herein, the term "adhere" is meant to refer to ionic, covalent, electrostatic, or other chemical attachment of a compound, product or composition to a substrate.

As used herein, the term "antimicrobially enhancing" refers to the use of the compounds, products, or compositions of the present invention, preferably those wherein the organosilane has antimicrobial activity, along with other ingredients, surfactants, fillers, wetting agents, pigments, dyes, antimigrants, etc., to create a composition or solution capable of fulfilling its original purpose, based upon the other ingredients, and also of providing antimicrobial protection during the particular application. The term "enhance" refers to the addition of antimicrobial activity to such compositions or solutions where no such activity previously existed, or to the increase of antimicrobial activity wherein the starting compositions or solutions inherently possessed antimicrobial activity.

As used herein, "hydrolyzable" refers to whether the moiety is capable of or prone to hydrolysis (i.e., splitting of the molecule or moiety into two or more new molecules or moieties) in aqueous or other suitable media. Conversely, "nonhydrolizable" refers to moieties that are not prone to or capable of hydrolysis in aqueous or other suitable media.

As used herein, "cationic" is used to refer to any compound, ion or moiety possessing a positive charge. Moreover, "anionic" is used to refer to any compound, ion or moiety possessing a negative charge. Furthermore, "monovalent" and "divalent" are used to refer to moieties having valances of one and two, respectively. Moreover, as used herein, the term "salt" is meant to apply in its generally defined sense as "compound formed by replacing all or part of the hydrogen ions of an acid with one or more cations of a base." See, e.g., American Heritage Dictionary, Definition of "Salt" (1981). Therefore, suitable salts for the present invention may be formed by replacing a hydrogen ion of a moiety with a cation, such as $K^+$, $Na^+$, $Ca^{2+}$, $Mg^{2+}$, etc. In addition, other suitable methods of generating salts are specified throughout this specification and are within the scope of the present definition. It is believed that, for the purposes of the present invention, the specific identity of the cation used for forming the salt is of lesser importance than the chemical structure of the anion of which the salt is formed.

As used herein, "food article" refers to perishable or nonperishable foods such as meats, fruits and vegetables, and also refers to other foods such as grains and dairy products. In preferable embodiments, the food articles referred to herein are those which are perishable or prone to spoilage upon exposure to microbes or other pathogens. In addition, a "consumable product" is meant to refer to food articles, fluids for drinking, medicines for ingestion or any other product introduced internally via any means into a human or animal.

As used herein, the term "antimicrobial" is used in its general sense to refer to the property of the described compound, product, composition or article to prevent or reduce the growth, spread, formation or other livelihood of organisms such as bacteria, viruses, protozoa, molds, or other organisms likely to cause spoilage or infection.

As used herein, the term "medical article" is used to refer to any suitable substrate which is or may come into contact with medical patients (human or animal), medical caregivers, bodily fluids, or any other source of contamination or infection generally associated with hospitals, clinics, physician's offices, etc.

As used herein, the term "stabilizer" is used to refer to the class of polyols as specified herein wherein any two of the at least three hydroxy groups are separated by at least three atoms. Such compounds have been found to stabilize the organosilanes of the invention by preventing self-condensation or other inactivation of the resulting compounds and products.

Finally, there terms "halogen" are used to refer to Fluorine "F", Chlorine "Cl", Bromine "Br", Iodine "I", and Astatine "At". Preferably, halogen or halide refers to F, Cl, or Br. The term "halide" is meant to include these halogens.

With these definitions in mind, the present invention provides the product formed from reacting an organosilane of the formula $R_nSiX_{4-n}$, where n is an integer of from 0 to 3, preferably 0 to 2; each R is, independently, a nonhydrolizable organic group; and each X is, independently, a hydrolyzable group, with a polyol containing at least three hydroxy groups, wherein any two (i.e., any selected combination of two hydroxy groups from all of the possible pairs of two such groups) of the at least three hydroxy groups are separated by at least three intervening atoms.

More preferably, in the above product, n is an integer from 0 to 2, preferably 1; each R is, independently, alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms; alkyl alcohol of similar carbon lengths, branching and substitution, or aromatic, such as benzyl, phenyl, etc.; each X is, independently, hydroxy, alkoxy, halogen (such as, but not limited to, Cl, Br, I, or F), acetyl, acetoxy, acyl, a hydroxylated solid or liquid polymeric moiety, polyether or polyalkylether; and the polyol is of the formula I:

$$[R_{11}(W)_p][R_{33}]_{3-o}C[(CH_2)_qOH]_o \qquad (I)$$

wherein o is an integer of from 2 to 3; q is an integer of from 1 to 2; p is an integer of from 0 to 1, preferably 0; W is alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms, polyether, aryl, preferably phenyl or benzyl, unsubstituted or substituted or heteroaryl, substituted with one or more of N, O, or S, preferably from 1 to 2 of N, O, or S, more preferably from 1 to 2 of N; $R_{11}$, and $R_{33}$ are, independently, halogen, such as Cl, Br, F, or I, H, $CH_2OH$, $N(CH_2CH_2OH)_2CH_3{}^+V^-$, $NH_2$, $NO_2$, $N(H)(CH_2)_3OSO_3H$, $N^+(CH_3)_2(CH_2)_3SO_3{}^+$, $N(CH_3)_3{}^+V^-$, $(CH_2)OPO_3H_2$, $(CH_2)PO_3H_2$, $N(H)R_{34}(CF_2)_eCF_3$ where e is an integer of from 1 to about 22, preferably of from 10 to 20, more preferably of from 14 to 18, and $R_{34}$ is CO or $SO_2$, $(W)_pZO$ where Z is H, alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms, aryl, preferably phenyl or benzyl, or heteroaryl, substituted with one or more of N, O, or S, preferably from 1 to 2 of N, O, or S, more preferably from 1 to 2 of N; $(W)_pZS(O)_r$ where Z is H, Na, a suitable mono- or di-valent cation, such as K, Mg, or Ca, alkyl, aryl, or heteroaryl as described above and r is an integer from 0 to 2, $(W)_pZ_1Z_2N$ where $Z_1$ and $Z_2$ are, independently, H, alkyl, aryl, or heteroaryl as described above, $(W)_pZ_3Z_4Z_5N^+Q^-$ where $Z_3$, $Z_4$, and $Z_5$ are, independently, H, alkyl, aryl, or heteroaryl as described above, or $(W)_pZ_6PO_3$ where $Z_6$ is H, Na, a suitable mono- or di-valent cation, alkyl, aryl, or heteroaryl as described above; $V^-$ is a suitable anionic moiety to form the salt of the compound of formula I. In a preferable embodiment, $V^-$ is halide, sulfate, tosylate, carboxylate, polycarboxylate, alkyl, arylsulfonate, phosphate, phosphonate, borate, or boronate.

In yet another embodiment, W is alkyl of from 1 to 22 carbon atoms, more preferably, of from 1 to 10 carbon atoms, even more preferably from 1 to 3 carbon atoms. In an alternate embodiment, W is polyether, more preferably a polypropyleneglycol or a polyethyleneglycol. In yet another alternate embodiment, W is aryl, preferably, phenyl or benzyl. In yet a further embodiment, W is heretoraryl, wherein the one or more heteroatoms are, independently, N, O, or S.

In a further embodiment of the present invention, the invention provides the product described above, wherein the organosilane is of the formula II, III, IV, or V:

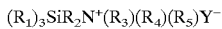  (II)

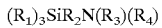  (III)

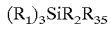  (IV)

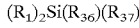  (V)

wherein each $R_1$ of the three is, independently, halogen or $R_6O$, where $R_6$ is H, alkyl of from 1 to about 6 carbon atoms, preferably of from 1 to 4 carbon atoms, more preferably of from 1 to 2 carbon atoms, acetyl, acetoxy, or acyl; $R_{35}$ is H, halogen (such as Cl, Br, F, or I), $NH_2(CH_2)_2NHR_2$, $NH_2R_2$, $C_3H_5O_2R_2$, $C_4H_5O_2R_2$, $NaO(CH_3O)P(O)R_2$, or $ClCH_2C_6H_4R_2$; $R_{36}$ and $R_{37}$ are, independently, halogen, H, alkyl of from 1 to about 8 carbon atoms, preferably of from 1 to 4 carbon atoms, more preferably of from 1 to 2 carbon atoms, isobutyl, phenyl, or n-octyl, $R_2$ is benzyl, vinyl or alkyl of from 1 to about 3 carbon atoms $R_3$ and $R_4$ are, independently, lower alkyl alcohol of from 1 to 4 carbon atoms, lower alkoxy of from 1 to 4 carbon atoms, alkyl of from 1 to about 22 carbon atoms, preferably 1 to about 10 carbon atoms, more preferably alkyl of from 1 to 4 carbon atoms, or more preferably of from 1 to 2 carbon atoms; or $R_3$ and $R_4$ can, together, form a morpholine or cyclic or heterocyclic, unsaturated or saturated, five to seven-membered ring of the formula VI:

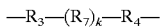  (VI)

where k is an integer from 0 to 2, preferably 0 to 1, most preferably 1, $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), where each $R_8$, $R_9$, and $R_{10}$ is, independently, benzyl, polyether, lower alkyl alcohol of from 1 to 4 carbon atoms, lower alkoxy of from 1 to 4 carbon atoms, or alkyl of from 1 to about 22 carbon atoms, preferably 1 to about 10 carbon atoms, and the "alkyl" specified above is of from 1 to 22 carbon atoms, more preferably of from 1 to 10 carbon atoms, most preferably of from 1 to 3 carbon atoms, the "aryl" is more preferably phenyl or benzyl, and $R_7$, where the ring is unsaturated is, CH, N, $N^+H$, $N^+(alkyl)$, $N^+(aryl)$, $N^+(benzyl)$, $N-CH_2-N$, $N^+H-CH_2-N$, $N^+(alkyl)-CH_2-N$, $N^+(aryl)-CH_2-N$, or $N^+(benzyl)-CH_2-N$ where the alkyl, aryl, or benzyl is as described above; wherein the ring is unsubstituted or substituted with alkyl of from 1 to 22 carbon atoms, more preferably of from 1 to 10 carbon atoms, most preferably of from 1 to 3 carbon atoms, ester, aldehyde, carboxylate (preferably acetoxy, acetyl, acyl or perfluorocarboxylate), amide, thionamide, nitro, amine, or halide, most preferably Cl, Br, or I; $R_5$ is lower alkyl alcohol, preferably of from 1 to 6 carbon atoms, more preferably of from 1 to 4 carbon atoms, $CH_2C_6H_5$, polyether, such as a polyethyleneglycol or a polypropylene glycol, alkyl of from 1 to 22 carbon atoms, more preferably of from 1 to 10 carbon atoms, most preferably of from 1 to 6 carbon atoms, alkoxy, of from 1 to 22 carbon atoms, more preferably of from 1 to 10 carbon atoms, most preferably of from 1 to 6 carbon atoms, perfluoroalkyl, of from 1 to 22 carbon atoms, more preferably of from 1 to 10 carbon atoms, most preferably of from 1 to 6 carbon atoms, perfluoroalkylsulfonate, of from 1 to 22 carbon atoms, more preferably of from 1 to 10 carbon atoms, most preferably of from 1 to 6 carbon atoms, or perfluoroalkylcarboxylate; and $Y^-$ is a suitable anionic moiety to form the salt of the compound of formula II, III, IV or V; and where the polyol is of the formula I:

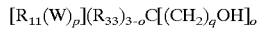  (I)

wherein o is an integer of from 2 to 3; q is an integer of from 1 to 2; p is an integer of from 0 to 1, preferably 0; W is alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms, polyether, aryl, preferably phenyl or benzyl, unsubstituted or substituted or heteroaryl, substituted with one or more of N, O, or S, preferably from 1 to 2 of N, O, or S, more preferably from 1 to 2 of N; $R_{11}$ and $R_{33}$ are, independently, halogen, such as Cl, Br, F, or I, H, $CH_2OH$, $N(CH_2CH_2OH)_2CH_3^+V^-$, $NH_2$, $NO_2$, $N(H)(CH_2)_3OSO_3H$, $N^+(CH_3)_2(CH_2)_3SO_3^-$, $N(CH_3)_3^+V^-$, $(CH_2)OPO_3H_2$, $(CH_2)PO_3H_2$, $N(H)R_{34}(CF_2)_eCF_3$ where e is an integer of from 1 to about 22, preferably of from 10 to 20, more preferably of from 14 to 18, and $R_{34}$ is CO or $SO_2$, $(W)_pZO$ where Z is H, alkyl, preferably of from 1 to 22 carbon atoms branched or unbranched, substituted or unsubstituted, more preferably of from 1 to 6 carbon atoms or from 10 to 20 carbon atoms, most preferably of from 1 to 4 carbon atoms or of from 14 to 18 carbon atoms, aryl, preferably phenyl or benzyl, or heteroaryl, substituted with one or more of N, O, or S, preferably from 1 to 2 of N, O, or S, more preferably from 1 to 2 of N; $(W)_pZS(O)_r$ where Z is H, Na, a suitable mono- or di-valent cation, such as K, Mg, or Ca, alkyl, aryl, or heteroaryl as described above and r is an integer from 0 to 2, $(W)_pZ_1Z_2N$ where $Z_1$ and $Z_2$ are, independently, H, alkyl, aryl, or heteroaryl as described above, $(W)_pZ_3Z_4Z_5N^+Q^-$ where $Z_3$, $Z_4$, and $Z_5$ are, independently, H, alkyl, aryl, or heteroaryl as described above, or $(W)_pZ_6PO_3$ where $Z_6$ is H, Na, a suitable mono- or di-valent cation, alkyl, aryl, or heteroaryl as described above; $V^-$ is a suitable anionic moiety to form the salt of the compound of formula I. In a preferable embodiment, each of Y and V is, independently, halide, sulfate, tosylate, carboxylate, polycarboxylate, alkyl, arylsulfonate, phosphate, phosphonate, borate, or boronate.

In a further embodiment, the present invention provides the product as described above wherein the polyol is a compound having the formula VII:

$$(R_{12})(R_{13})C[(CH_2)_sR_{14}]_2 \qquad (VII)$$

wherein s is an integer of from 1 to 2; $R_{12}$ is $(CH_2)_gR_{14}$ where g is an integer of from 0 to 10, preferably of from 1 to 6, and more preferably of from 1 to 3, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(CH_3)_3T^-$, $N^-(R_{17})(R_{18})(R_{19})T^-$, where $R_{15}R_{16}$, $R_{17}$, and $R_{18}$ are independently, H, O, or lower alkyl of from 1 to about 4 carbon atoms, polyalkyl ester, benzyl, or $R_{15}$ and $R_{16}$, together, or $R_{17}$ and $R_{18}$, together, may, independently, form an amide, sulfonamide, phosphonamide, oxime, thionamide, quaternary ammonium, imine, imide, guanidine, piperazine, morpholine, or $N(O)R_{20}R_{21}$, where $R_{20}$ and $R_{21}$ are, independently, lower alkyl alcohol of from 1 to 4 carbon atoms, lower alkoxy of from 1 to 4 carbon atoms, or alkyl of from 1 to about 4 carbon atoms; $R_{19}$ is H or alkyl of from 1 to about 22 carbon atoms, more preferably of from 1 to 10 carbon atoms, and even more preferably of from 1 to 6 carbon atoms; and $T^-$ is a suitable anionic moiety to form a quaternary ammonium salt of the compound of formula VII; $R_{13}$ is H, OH, $(CH_2)_sR_{14}$, $(CH_2)OPO_3H_2$, or $(CH_2)PO_3H_2$, lower alkyl of from 1 to 4 carbon atoms, lower alkoxy of from 1 to about 4 carbon atoms; and each $R_{14}$ is, independently, OH or $[-CH_2C(CH_2OH)_2CH_2O]_j-H$ where j is an integer of from 0 to 5, preferably of from 0 to 2, more preferably 0, and wherein one of the $R_{14}$ moieties is bonded to the Si by removal of the hydrogen from a hydroxy such that the oxygen of the hydroxy is bonded to Si; or a perfluoro- analog, i.e, wherein one or more of the hydrocarbon H atoms are replaced with F atoms; or a mixture thereof In a preferred embodiment of the above product, g is an integer of from 0 to 3; $R_{12}$ is $(CH_2)_gR_{14}$, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(CH_3)_3T^-$, or $N^+(R_{17})(R_{18})(R_{19})T^-$; $R_{13}$ is H, OH, $(CH_2)_sR_{14}$, $(CH_2)OPO_3H_2$, or $(CH_2)PO_3H_2$, lower alkyl of from 1 to 4 carbon atom lower alkoxy of from 1 to about 4 carbon atoms, and each $R_{14}$ is, independently, OH or $[-CH_2C(CH_2OH)_2CH_2O]_j-H$ where j is an integer of from 0 to 5 and wherein one of the $R_{14}$ moieties is bonded to the Si by removal of the hydrogen from a hydroxy such that the oxygen of the hydroxy is bonded to Si. In a further preferred embodiment, $R_{12}$ is $(CH_2)_gR_{14}$, lower alkyl of from 1 to about 4 carbon atoms, or lower alkoxy of from 1 to about 4 carbon atoms. In an alternate preferred embodiment, $R_{12}$ is $N(R_{15})(R_{16})$, $N(H)(CH_2)_3OSO_3H$, $N(H)(CH_2)_3OSO_3H$, $N^+(H)(CH_2)_3OSO_3H$, $N^+(CH_3)_2(CH_2)_3SO_3^-$, $N^-(CH_3)_3T^-$, or $N^+(R_{17})(R_{18})(R_{19})T^-$.

In another embodiment of the above-described product, g is an integer of from 0 to 3; $R_{12}$ is $(CH_2)_gR_{14}$, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(R_{17})R_{18}(R_{19})T^-$; and each $R_{14}$ is OH. In a further, alternate embodiment, g is an integer of from 0 to 3; $R_{12}$ is $(CH_2)_gR_{14}$, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^-(CH_3)_2(CH_2)_3SO_3^-$, $N^+(CH_3)_3T^-$, or $N^+(R_{17})(R_{18})(R_{19})T^-$; and each $R_{14}$ is, independently, $[-CH_2C(CH_2OH)_2CH_2O]_j-H$ where j is an integer of from 0 to 5 and wherein one of the $R_{14}$ moieties is bonded to the Si by removal of the hydrogen from a hydroxy such that the oxygen of the hydroxy is bonded to Si.

In another embodiment, the present invention provides a compound having the formula $(R)_nSi(X)_{4-n-y}(R_{41})_y$ wherein n is an integer of from 0 to 3; y is an integer of from 1 to 4; each R is, independently, a nonhydrolizable organic group, preferably a quaternary ammonium moiety; each X is, independently, a hydrolyzable group, preferably methoxy or ethoxy; and each $R_{41}$ is, independently, a polyol containing at least three hydroxy groups, wherein any two of the at least three hydroxy groups are separated by at least three intervening atoms and wherein the polyol is bonded to the Si by removal of the hydrogen from one of the at least three hydroxy groups such that the oxygen of the one of the at least three hydroxy groups is bonded to Si.

In a further embodiment, the present invention provides a compound having the formula VIII, IX, X or XI:

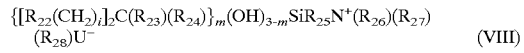 (VIII)

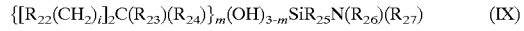 (IX)

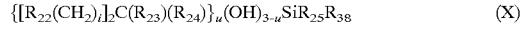 (X)

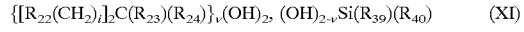 (XI)

wherein m is an integer of from 1 to 3, preferably 3; i is an integer of from 1 to 2, preferably 1; u is an integer of from 0 to 3; v is an integer of from 0 to 2; each $R_{22}$ is, independently, H or $OR_{33}$ where $R_{33}$ is, independently, $[-CH_2C(CH_2OH)_2CH_2O]_f-H$ where f is an integer of from 0 to 5, preferably from 0 to 2, more preferably 0; $R_{38}$, is H, halogen (such as Cl, Br, or I), $NH_2(CH_2)_2NHR_{25}$, $NH_2R_{25}$, $C_3H_5O_2R_{25}$, $C_4H_5O_2R_{25}$, $NaO(CH_3O)P(O)R_{25}$, or $ClCH_2C_6H_4R_{25}$; $R_{39}$ and $R_{40}$ are, independently, halogen (such as Cl, Br, or I), H, alkyl of from 1 to about 8 carbon atoms, preferably of from 1 to 3 carbons, isobutyl, phenyl, or n-octyl; $R_{23}$ and $R_{24}$ are, independently, halogen (Cl, Br, or I), H, $CH_2OH$, $N(CH_2CH_2OH)_2CH_3^+Q^-$, $NH_2$, $NO_2$, $N(H)(CH_2)_3OSO_3H$, $N^+(CH_3)_2(CH_2)_3SO_3^-$, $N(CH_3)_3^+Q^-$, $(CH_2)OPO_3H_2$, $(CH_2)PO_3H_2$, $N(H)R_{34}(CF_2)_eCF_3$ where e is an integer of from 1 to about 22, preferably from 1 to about 10 and more preferably from 1 to 4 and $R_{34}$ is CO or $SO_2$, $(W)_pZO$ where Z is H, alkyl, aryl, or heteroaryl as described above, $(W)_pZS(O)_r$ where Z is H, Na, a suitable mono- or di-valent cation, alkyl, aryl, or heteroaryl as described above and r is an integer from 0 to 2, $(W)_pZ_1Z_2N$ where $Z_1$ and $Z_2$ are, independently, H, alkyl, aryl, or heteroaryl as described above, $(W)_pZ_3Z_4Z_5N^+Q^-$ where $Z_3$, $Z_4$, and $Z_5$ are, independently, H, alkyl, aryl, or heteroaryl as described above, or $(W)_pZ_6PO_3$ where $Z_6$ is H, Na, a suitable mono- or di-valent cation, alkyl, aryl, or heteroaryl as described above; where p is an integer from 0 to 1, preferably 0; W is alkyl, preferably of from 1 to 22 carbon atoms, more preferably of from 1 to 6 or 10 to 20 carbon atoms, most preferably of from 1 to 4 or 14 to 18 carbon atoms, polyether, preferably a polyethyleneglycol or polypropylene glycol, aryl, preferably benzyl or phenyl, or heteroaryl, wherein the heteroatom is preferably one or more of N, S, or O, and $Q^-$ is a suitable anionic moiety to form the salt of the compound of formula VIII, IX, X, or XI; $R_{25}$ is benzyl, vinyl, or alkyl of from 1 to about 3 carbon atoms; $R_{26}$ and $R_{27}$ are, independently, lower alkyl alcohol, preferably of from 1 to 6 carbon atoms, more preferably of from 1 to 3 carbon atoms, lower alkoxy of from 1 to 4 carbon atoms, alkyl of from 1 to about 22 carbon atoms, preferably 1 to about 10 carbon atoms or $R_{26}$ and $R_{27}$ can, together, form a morpholine or cyclic or heterocyclic, unsaturated or saturated, five to seven-membered ring of the formula XII:

$$-R_{26}-(R_{29})_h-R_{27}- \qquad (XII)$$

where h is an integer from 0 to 2, preferably 1, and $R_{29}$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_{30})(R_{31})(R_{32})$, N(alkyl), N(aryl), N(benzyl) where $R_{30}$, $R_{31}$, and $R_{32}$ are, independently, benzyl, polyether, lower alkyl alcohol, lower alkoxy of from 1 to 4 carbon atoms, alkyl of from 1 to about 22 carbon atoms, preferably 1 to about 10 carbon atoms, and where the alkyl, aryl and benzyl are as described above, and $R_{29}$, where the ring is unsaturated is, CH, N, $N^+H$, $N^+$(alkyl), $N^+$(aryl), $N^+$(benzyl), $N-CH_2-N$, $N^+H-CH_2-N$, $N^+$(alkyl)—$CH_2-N$, $N^+$(aryl)—$CH_2-N$, or $N^+$(benzyl) —$CH_2-N$ and where alkyl, aryl and benzyl are as described above; wherein the ring is unsubstituted or substituted with alkyl of from 1 to 22 carbon atoms, preferably of from 1 to 10 carbon atoms, more preferably of from 1 to 6 carbon atoms, and most preferably of from one to 3 carbon atoms, ester, aldehyde, carboxylate, amide, thionamide, nitro, amine, or halide; $R_{28}$ is lower alkyl alcohol, preferably of from 1 to 6 carbon atoms, more preferably of from 1 to 3 carbon atoms, $CH_2C_6H_5$ polyether, preferably a polyethylene glycol or polypropylene glycol, alkyl, alkoxy, perfluoroalkyl, perfluoroalkylsulfonate, or perfluoroalkylcarboxylate wherein the alkyl, alkoxy, perfluoroalkyl, perfluoroalkylsulfonate, or perfluoroalkylcarboxylate is of from 1 to about 22 carbon atoms, preferably of from 1 to 10 carbon atoms and more preferably of from 1 to 6 carbon atoms; and $U^-$ is a suitable anionic moiety to form the salt of the compound of formula XII. In a further preferred embodiment, each of Q and U is, independently, halide, sulfate, tosylate, carboxylate, polycarboxylate, alkyl, arylsulfonate, phosphate, phosphonate, borate, or boronate.

In a further embodiment, the compound is of the formula VIII. In a further embodiment, the compound is of the formula IX. In another further embodiment, the compound is of the formula X. In yet another further embodiment, the compound is of the formula XI.

In an alternate further embodiment, the present invention provides the compound as described above, wherein $R_{22}$ is H or OH. In a further embodiment, the present invention provides the compound as described above, wherein $R_{23}$ and $R_{24}$ are, independently, halogen, H, $CH_2OH$, $N(CH_2CH_2OH)_2CH_3^+Q^-$, $NH_2$, $NO_2$, $N(H)(CH_2)_3OSO_3H$, $N^+(CH_3)_2(CH_2)_3SO_3^-$, $N(CH_3)_3^+Q^-$, $(CH_2)OPO_3H_2$, $(CH_2)PO_3H_2$. In an alternate embodiment, $R_{23}$ and $R_{24}$ are, independently, $N(H)R_{34}(CF_2)_eCF_3$. In yet another embodiment, $R_{23}$ and $R_{24}$ are, independently, $(W)_pZO$. In a further embodiment, $R_{23}$ and $R_{24}$ are, independently, $(W)_pZS(O)_r$. Alternatively, $R_{23}$ and $R_{24}$ are, independently, $(W)_pZ_1Z_2N$. Moreover, in another alternate embodiment, $R_{23}$ and $R_{24}$ are, independently, $(W)_pZ_3Z_4Z_5N^+Q^-$. In yet another embodiment, $R_{23}$ and $R_{24}$ are, independently, $(W)_pZ_6PO_3$. Moreover, in another embodiment, $R_{26}$ and $R_{27}$ are, independently, lower alkyl alcohol, lower alkoxy of from 1 to 4 carbon atoms, or alkyl of from 1 to about 22 carbon atoms, preferably 1 to about 10 carbon atoms, preferably of from 1 to 4 carbon atoms. In an alternate embodiment, $R_{26}$ and $R_{27}$ together, form a morpholine or cyclic or heterocyclic, unsaturated or saturated, five to seven-membered ring of the formula XII and $R_{29}$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_{30})(R_{31})(R_{32})$, N(alkyl), N(aryl), N(benzyl) where $R_{30}$, $R_{31}$, and $R_{32}$ are, independently, benzyl, polyether, lower alkyl alcohol, lower alkoxy of from 1 to 4 carbon atoms, alkyl of from 1 to about 22 carbon atoms, preferably 1 to about 10 carbon atoms, and $R_{29}$, where the ring is unsaturated is, CH, N, $N^+H$, $N^+$(alkyl), $N^+$(aryl), $N^+$(benzyl), $N-CH_2-N$, $N^+H-CH_2-N$, $N^+$(alkyl)—$CH_2-N$, $N^+$(aryl)—$CH_2-N$, or $N^+$(benzyl)—$CH_2-N$; wherein the ring is unsubstituted or substituted with alkyl of from 1 to 22 carbon atoms, ester, aldehyde, carboxylate, amide, thionamide, nitro, amine, or halide as described above. Alternatively, $R_{26}$ and $R_{27}$ together, form a morpholine or cyclic or heterocyclic, saturated, five to seven-membered ring of the formula XII and $R_{29}$ is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_{30})(R_{31})(R_{32})$, N(alkyl), N(aryl), N(benzyl) where $R_{30}$, $R_{31}$, and $R_{32}$ independently, benzyl, polyether, lower alkyl alcohol, lower alkoxy of from 1 to 4 carbon atoms, alkyl of from 1 to about 22 carbon atoms, preferably 1 to about 10 carbon atoms. In yet another embodiment, $R_{26}$ and $R_{27}$ can, together, form a morpholine or cyclic or heterocyclic, unsaturated, five to seven-membered ring of the formula XII and $R_{29}$ is, CH, N, $N^+H$, $N^+$(alkyl), $N^+$(aryl), $N^+$(benzyl), $N-CH_2-N$, $N^+H-CH_2-N$, $N^+$(alkyl)—$CH_2-N$, $N^+$(aryl)—$CH_2-N$, or $N^+$(benzyl)—$CH_2-N$. In a further embodiment, the ring is unsubstituted or substituted with alkyl of from 1 to 22 carbon atoms, ester, aldehyde, carboxylate, amide, thionamide, nitro, amine, or halide.

Moreover, in yet another embodiment, $R_{28}$, is lower alkyl alcohol, $CH_2C_6H_5$, alkyl, alkoxy. In an alternate embodiment, $R_{28}$ is polyether. In yet another alternate embodiment, $R_{28}$ is perfluoroalkyl, perfluoroalkylsulfonate, or perfluoroalkylcarboxylate.

Moreover, in a further embodiment, the present invention provides a compound having the formula XIII:

$$(R_{42})(R_{43})(R_{44})SiR_{45}N^+(R_{46})_2(R_{47})X^- \qquad (XIII)$$

wherein X is halogen such as Cl, Br, or 1, preferably Cl; $R_{45}$ is lower alkyl of from 1 to 3 carbon atoms, preferably 3 carbon atoms; $R_{46}$ is lower alkyl of from 1 to 3 carbon atoms, preferably 1 carbon atoms; $R_{47}$ is alkyl of from 1 to 22 carbon atoms, preferably of from 10 to 20 carbon atoms, more preferably of from 14 to 18 carbon atoms and most preferably of 18 carbon atoms; $R_{42}$, $R_{43}$ and $R_{44}$ are, independently, OH, $CH_2OH$, or $(-OCH_2)C(Z)(R_6)(R_7)$, wherein each Z is, independently, $-CH_2OH$, $-CH_3$, $-NH_2$, $-NO_2$, $-(CH_2)OPO_3H_2$, $-(CH_2)PO_3H_2$, $-N^+(CH_3)_3Cl^-$, $N(H)(CH_2)_3OSO_3H$, or $N^+(CH_3)_2(CH_2)_3SO_3^-$, provided that at least one of $R_{42}$, $R_{43}$, and $R_{44}$ is not OH or $CH_2OH$.

In another embodiment, the present invention provides the compound of formula XIII wherein $R_{47}$ is $C_{18}H_{37}$. In an alternate embodiment, $R_{42}$, $R_{43}$, and $R_{44}$ are, independently, OH, $CH_2OH$, or $-OCH_2-C(CH_2OH)_3$. In another alternate embodiment, $R_{42}$, $R_{43}$, and $R_{44}$ are, independently, OH, $CH_2OH$, or $-OCH_2C(CH_2OH)_2(CH_3)$. In a further alternate embodiment, $R_{42}$, $R_{43}$, and $R_{44}$ are, independently, OH, $CH_2OH$, or $-OCH_2C(CH_2OH)_2(NH_2)$. In another alternate embodiment, $R_{42}$, $R_{43}$, and $R_{44}$ are, independently, OH, $CH_2OH$, or $-OCH_2C(CH_2OH)_2(NO_2)$. In another alternate embodiment, $R_{42}$, $R_{43}$, and $R_{44}$ are, independently, OH, $CH_2OH$, or $-OCH_2C(CH_2OH)_2[(CH_2)OPO_3H_2]$. In another alternate embodiment, $R_{42}$, $R_{43}$, $R_{44}$ are independently, OH, $CH_2OH$, or $OCH_2C(CH_2OH)_2[(CH_2)_2)PO_3H_2]$. In another alternate embodiment, $R_{42}$, $R_{43}$, and $R_{44}$ are, independently, OH, $CH_2OH$, or $-OCH_2C(CH_2OH)_2[N^+(CH_3)_3]Cl^-$. In another alternate embodiment, $R_{42}$, $R_{43}$, and $R^{44}$ are, independently, OH, $CH_2OH$, or $—OCH_2C(CH_2OH)_2[N(H)(CH_2)_3OSO_3H]$. In another alternate embodiment, $R_{42}$, $R_{43}$, and $R_{44}$ are, independently, OH, $CH_2OH$, or $—OCH_2C(CH_2OH)_2[N^+(CH_2)SO_3]$.

Moreover, in a further embodiment, the present invention provides, a water stable composition, comprising the product as described above and water. In a further embodiment, the invention also provides a water stable composition, comprising one or more of the compounds as described above and water.

In a further preferred embodiment of the product, the organosilane is 3-(trihydroxysilyl)propyldimethyloctadecyl ammonium chloride and the polyol is pentaerythritol. In a further preferred embodiment, the organosilane is 3-(trihydroxysilyl)propyldimethyloctadecyl ammonium chloride and the polyol is tris(hydroxymethyl)ethane. In yet a further preferred embodiment, the organosilane is 3-(trihydroxysilyl)prop), dimethyloctadecyl ammonium chloride and the polyol is dipentaerythritol, tripentaerythritol, tetrapentaerythritol, tris(hydroxymethyl) propane, tris(hydroxymethyl)nitromethane, tris (hydroxymethyl)aminomethane, or tris(hydroxymethyl) methanetrimethyl ammonium iodide.

In addition, the present invention also provides a composition for treating a substrate, comprising a carrier and an effective amount of the product as described above. In an alternate embodiment, the present invention provides a composition for treating a substrate, comprising a carrier and an effective amount of the compound as described above. In further embodiments, the carrier is other than water.

In a further embodiment of the product as described above, the organosilane is 3-(trimethoxysilyl) propyldimethyloctadecyl ammonium chloride, 3-(trimethoxysilyl)propylmethyldi(decyl)ammonium chloride, 3-chloropropyltrimethylsilane, 3-chloropropyltrimethoxysilane, octadecyltrimethoxysilane, or perfluorooctyltriethoxysilane and the polyol is pentaerythritol, dipentaerythritol, tripentaerythritol, tetrapentaerythritol, tris(hydroxymethyl)ethane, tris (hydroxymethyl)propane, tris(hydroxymethyl) nitromethane, tris(hydroxymethyl)aminomethane, or tris (hydroxymethyl)methanetrimethyl ammonium iodide. In yet another embodiment, the organosilane is $(CH_3O)_3Si(CH_2)_3 N^+(CH_3)_2C_{18}H_{37}Br^-$, $(CH_3O)_3Si(CH_2)_3N^+(C_{10}H_{21}) CH_3Cl^-$, $(CH_3O)_3Si(CH_2)_3N^+(CH_{10}H_{21})CH_3Br^-$, $(CH_3O)_3 Si(CH_2)_3N^+(CH_3)_3Cl^-$, $(CH_3O)_3Si(CH_2)_3N^+(CH_3)_2 C_8H_{17}Cl^-$, $(CH_3O)_3Si(CH_2)_3N^+(CH_3)_2C_{10}H_{21}Cl^-$, $(CH_3O)_3 Si(CH_2)_3N^+(CH_3)_2C_{12}H_{25}Cl^-$, $(CH_3O)_3Si(CH_2)_3N^+(CH_3)_2 C_{14}H_{29}Cl^-$, $(CH_3O)_3Si(CH_2)_3N^+(CH_3)_2C_{16}H_{33}Cl^-$, $(CH_3O)_3 Si(CH_2)_3N^+(CH_3)_2C_{20}H_{41}Cl^-$, $(CH_3O)_3Si(CH_2)_3 N^+(C_4)H_9)_3Cl^-$, $(CH_3O)_3Si(CH_2)_3N^+(C_2H_5)_3Cl^-$, $(CH_3CH_2O)_3Si(CH_2)_3N^+(CH_3)_2C_{18}H_{27}Cl^-$, $(CH_3O)_3Si (CH_2)_3NHC(O)(CF_2)_6CF_3$, $(CH_3O)_3Si(CH_2)_3NHC(O) (CF_2)_8CF_3$, $(CH_3O)_3Si(CH_2)_3NHC(O)(CF_2)_{10}CF_3$, $(CH_3O)_3 Si(CH_2)_3NHC(O)(CF_2)_{12}CF_3$, $(CH_3O)_3Si(CH_2)_3 NHC(O)(CF_2)_{14}CF_3$, $(CH_3O)_3Si(CH_2)_3NHC(O)(CF_2)_{16} CF_3$, $(CH_3O)_3Si(CH_2)_3NHSO_2(CF_2)_7CF_3$, $(CH_3O)_3Si (CH_2)_3 N^+(CH_3)_2(CH_2)_3NHC(O)(CH_2)_6CH_3$, $(CH_3O)_3Si (CH_2)_3 N^+(CH_3)_2(CH_2)_3NHC(O)(CH_2)_8CH_3$, $(CH_3O)_3Si (CH_2)_3 N^+(CH_3)_2(CH_2)_3NHC(O)(CH_2)_{10}CH_3$, $(CH_3O)_3Si (CH_2)_3 N^+(CH_3)_2(CH_2)_3NHC(O)(CH_2)_{12}CH_3$, $(CH_3O)_3Si (CH_2)_3 N^+(CH_3)_2(CH_2)_3NHC(O)(CH_2)_{14}CH_3$, $(CH_3O)_3Si (CH_2)_3 N^+(CH_3)_2(CH_2)_3NHC(O)(CH_2)_{16}CH_3$, $(CH_3O)_3Si (CH_2)_3 N^+(CH_3)_2(CH_2)_3NHC(O)(CF_2)_6CF_3$, $(CH_3O)_3Si (CH_2)_3N^+(CH_3)_2(CH_2)_3NHC(O)(CF_2)_8CF_3$, $(CH_3O)_3Si (CH_2)_3N^+(CH_3)_2(CH_2)_3NHC(O)(CF_2)_8CF_3$, $(CH_3O)_3Si (CH_2)_3N^+(CH_3)_2(CH_2)_3NHC(O)(CF_2)_{12}CF_3$, $(CH^3O)_3Si (CH_2)_3N^+$ $(CH_3)_2(CH_2)_3NHC(O)(CF_2)_{14}CF_3$, $(CH_3O)_3Si(CH_2)_3N^+$ $(CH_3)_2(CH_2)_3NHC(O)(CF_2)_{16}CF_3$, $(CH_3O)_3Si(CH_2)_3N^+$ $(CH_3)_2(CH_2)_3NHSO_2(CF_2)_7CF_3$, $(CH_3O)_3Si(CH_2)_3N^+$ $(CH_3)_2(CH_2)_3NHSO_2(CF_2)_9CF_3$, $(CH_3O)_3Si(CH_2)_3N^+$ $(CH_3)_2(CH_2)_3NHSO_2(CF_2)_{11}CF_3$, $(CH_3O)_3Si(CH_2)_3N^+$ $(CH_3)_2(CH_2)_3NHSO_2(CF_2)_{13}CF_3$, $(CH_3O)_3Si(CH_2)_3N^+$ $(CH_3)_2(CH_2)_3NHSO_2(CF_2)_{15}CF_3$, or $(CH_3O)_3Si(CH_2)_3N^+$ $(CH_3)_2(CH_2)_3NHSO_2(CF_2)_{16}CF_3$. Moreover, in still another embodiment, the organosilane is $NH_2(CH_2)_2NH(CH_2)_3Si (OCH_3)_3$, $NH_2(CH_2)_3Si(OCH_3)_3$, $NH_2(CH_2)_3Si(OCH_3)_3$, $NH_2(CH_2)_3Si(OCH_2CH_3)_3$, $Cl(CH_2)_3Si(OCH_3)_3$, $Cl(CH_2)_3 Si(OCH_2CH_3)_3$, $Cl(CH_2)_3$, $SiCl_3$, $C_3H_5O_2(CH_2)_3Si(OCH_3)_3$, $C_3H_5O_2(CH_2)_3Si(OCH_2CH_3)_3$, $C_4H_5O_2(CH_2)_3Si(OCH_3)_3$, $C_4H_5O_2(CH_2)_3Si(OCH_2CH_3)_3$, $CH_3SiHCl_2$, $NaO(CH_3O)P(O)(CH_2)_3Si(OH)_3$, $SiHCl_3$, n-2-vinylbenzylamino-ethyl-3-aminopropyltrimethoxysilane HCL, $H_2C=CHSi(OCOCH_3)_3$, $H_2C=CHSi(OCH_3)_3$, $H_2C=CHSi(OCH_2CH_3)_3$, $H_2C=CHSiCl_3$, $(CH_3)_2SiCl_2$, $(CH_3)_2Si(OCH_3)_2$, $(C_6H_5)_2SiCl_2$, $(C_2H,)SiCl_3$, $(C_2H_5)Si (OCH_3)_3$, $(C_2H_5)Si(OCH_2CH_3)_3$, isobutyltrimethoxysilane, n-octyltriethoxysilane, $CH_3(C_6H_5)SiCl_2$, $CH_3SiCl_3$, $CH_3Si (OCH_3)_3$, $C_6H_5SiCl_3$, $C_6H_5Si(OCH_3)_3$, $C_3H_7SiCl_3$, $C_3H_7Si (OCH_3)_3$, $SiCl_4$, $ClCH_2C_6H_4CH_2CH_2SiCl_3$, $ClCH_2C_6H_4CH_2CH_2Si(OCH_3)_3$, $ClCH_2C_6H_4CH_2CH_2Si (OCH_2CH_3)_3$, decyltrichlorosilane, dichloromethyl(4-methylphenethyl)silane, diethoxymethylphenylsilane, [3-(diethylamino) propyl]trimethoxysilane, 3-(dimethoxymethylsilyl)-1-propanethiol, dimethoxymethylvinylsilane, 3-[tris(trimethylsilyloxy)silyl] propyl methacrylate, trichloro[4-(chloromethyl) phenyl] silane, methylbis (trimethylsilyloxy) vinylsilane, methyltripropoxysilane, or trichlorocyclopentylsilane.

In addition, the present invention provides a compound having the formula $(R)_n, Si(X)_{4-n-y}(R_{41})_y$ wherein n is an integer of from 0 to 3, preferably 0 to 2; y is an integer of from 1 to 4; each R is, independently, a nonhydrolizable organic group; each X is, independently, a hydrolyzable group; and each $R_{41}$ is, independently, a poly (tetrahydrofuran), a poly(vinyl)alcohol, hydroxyethyl cellulose, starch, or a cellulosic derivative, containing at least three hydroxy groups, wherein any two of the at least three hydroxy groups are separated by at least three intervening atoms and wherein the $R_{41}$ bonded to the Si by removal of the hydrogen from one of the at least three hydroxy groups such that the oxygen of the one of the at least three hydroxy groups is bonded to Si.

Moreover, the present invention also provides a product from reacting an organosilane of the formula II, III, IV, or V:

  (II)

  (III)

  (IV)

  (V)

as substantially previously described with reference to the formula numbers II, III, IV and V, with a poly (tetrahydrofuran), a poly(vinyl)alcohol, hydroxyethyl cellulose, starch, a cellulosic derivative, or a mixture thereof In yet a further embodiment, the present invention also provides a product produced as described above, but where the polyol is a phosphorylated pentaerythritol or a pentaerythritol substituted aryl. In a further embodiment, the polyol is of the formula XIV:

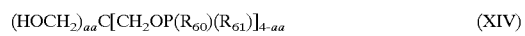  (XIV)

or is aryl, preferably phenyl, substituted with from 2 to 6 moieties of $—(OCH_2)C(CH_2OH)_3$, wherein the substitutions are ortho, meta, or para with respect to one another; wherein aa is an integer of from 0 to 4, preferably 1 to 2, more preferably 1; each $R_{60}$ is, independently, $O_2$ or OH; and each $R_{61}$ is, independently, H, a mono- or di-valent cation, such as, but not limited to, $K^+$, $Na^+$, $Ca^{+2}$, or $Mg^{+2}$, or $OR_{62}$ where $R_{62}$ is alkyl of from 1 to 22 carbon atoms, preferably of from 1 to 10 carbon atoms, more preferably lower alkyl of from 1 to 6 carbon atoms, or is lower alkyl alcohol of from 1 to 4 carbon atoms, or alkoxy of from 1 to 4 carbon atoms.

In addition, the present invention also provides a method of treating a substrate, comprising contacting the substrate with a sufficient amount of the product as described above for a period of time sufficient for treatment of the substrate. Moreover, in an alternate embodiment, the present invention provides a method of treating a substrate, comprising contacting the substrate with a sufficient amount of the compound as described above for a period of time sufficient for treatment of the substrate.

In addition, the present invention provides a treated substrate having adhered thereto the product as described above. Alternatively, the present invention provides a treated substrate having adhered thereto the compound as described above.

In yet another embodiment, the present invention provides a method of dyeing and treating a substrate, comprising contacting the substrate with an aqueous (i.e., substantially water soluble) composition comprising an aqueous soluble dye suitable for dyeing a substrate and the product formed from reacting an organosilane of the formula $R_nSiX_{4-n}$, where n is an integer of from 0 to 3, preferably 0 to 2; each R is, independently, a nonhydrolizable organic group, and each X is, independently, a hydrolyzable group, with a polyol containing at least three hydroxy groups, wherein any two of the at least three hydroxy groups are separated by at least three intervening atoms, for a period of time sufficient to dye and treat the substrate.

In a further preferred embodiment, the present invention provides a method of antimicrobially treating a food article, comprising contacting the food article with an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolizable group, with a polyol containing at least three hydroxy groups, wherein any two of the at least three hydroxy groups are separated by at least three intervening atoms, for a period of time sufficient to antimicrobially treat the food article.

In yet another embodiment, the present invention provides a method of antimicrobially coating a fluid container used for containing a human or animal consumable product, comprising contacting the container with an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to antimicrobially coat the container.

Moreover, in yet another embodiment, the present invention provides a method of antimicrobially coating a latex medical article for use in a human or animal medical procedure, comprising contacting the article with an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to antimicrobially coat the article. In a further embodiment of this method, the article is a surgical glove.

In yet another embodiment, the present invention provides a method of antimicrobially treating a substrate selected from the group consisting of a concrete pipe, a tooth brush, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from reacting an antimicrobial organosilane of the formula $R_nSiX_{4-n}$ where n is an integer of from 0 to 3, preferably 0 to 2; each R is, independently, a nonhydrolizable organic group; and each X is, independently, a hydrolyzable group, with a polyol containing at least three hydroxy groups, wherein any two of the at least three hydroxy groups are separated by at least three intervening atoms, for a period of time sufficient to antimicrobially treat the substrate.

Moreover, in yet another embodiment, the present invention provides a method of antimicrobially enhancing a product of grout, rubbing alcohol, a flower preservative, or a waterproofing solution, comprising admixing with the product an effective amount of the product formed from reacting an antimicrobial organosilane of the formula $R_nSiX_{4-n}$ where n is an integer of from 0 to 3, preferably 0 to 2; each R is, independently, a nonhydrolizable organic group, and each X is, independently, a hydrolyzable group, with a polyol containing at least three hydroxy groups, wherein any two of the at least three hydroxy groups are separated by at least three intervening atoms, for a period of time sufficient to antimicrobially enhance the product.

The present invention provides water-stabilized and solubilized organosilane compounds, products and compositions, methods for their use, and articles prepared using the compounds, products and compositions. In particular, the present invention is useful in stabilizing a broad variety of organosilanes of the general formula $R_nSiX_{4-n}$ where n is an integer of from 0 to 3, preferably 0 to 2; R is a nonhydrolizable organic group, such as but not limited to, alkyl, aromatic, organofunctional, or a combination thereof; and X is halogen, such as but not limited to, Cl, Br, or I, or X is hydroxy, alkoxy such as methoxy or ethoxy, acetoxy, or unsubstituted or substituted acyl. For such organosilanes, X is prone to react with various hydroxyl containing molecules to liberate methanol or ethanol. However, it is this reaction of X which is responsible for the instability and, often, water-insolubility of such organosilanes.

In a further embodiment, the present invention employs from about 0.001% to about 15% by weight of an organosilane containing hydrolyzable groups and from about 0.25 to about 5.0 molar equivalents, preferably from 1 to about 2 molar equivalents of a polyol stabilizer of the invention. The compounds, products and compositions of the present invention are prepared by admixing or dissolving any of the described polyol stabilizers in less than the final desired volume of water, adding the any of the desired organosilanes to the water solution, and then diluting further with water to the desired concentration. This preparation is preferably for water soluble stabilizers, such as pentaerythritol, tris (hydroxymethyl)ethane, tris(hydroxymethyl)nitromethane, etc. Alternatively, where the stabilizers are not sufficiently water-soluble, additional stability is achieved by directly forming a trioxasilabicyclooctyl species and the organosilane may be reacted with the stabilizer in a non-aqueous solvent. In such an alternative preparation, the remaining solvent (e.g., methanol) is liberated via distillation, as generally described in Example III below. Both of these methods provide stable, clear solutions of the organosilane which are capable of coating surfaces with the organosilane upon treatment of the surface with the solution. The solutions are stable within a pH range of from about 2.0 to about 10.5, preferably from about 2.0 to about 7.0, for extended periods, up to several months or longer. Higher pH stability (>7.0) is also within the scope of the present invention, as further separately described below. The solutions of the present invention are, in certain preferred embodiments, useful for the application of various organosilane coupling agents to surfaces in industrial and household uses without the use of toxic and/or flammable organic solvents. One of ordinary skill in the art would recognize that the above preparation steps are merely guidelines and such a person would, without undue experimentation, be able to prepare the composition by varying the reaction parameters and order of introduction of reagents and starting materials without deviating from the basic and novel characteristics of the present invention.

Silanes

The present invention is useful for stabilizing organosilanes of the general formula $R_nSiX_{4-n}$ where n is an integer of from 0 to 3, preferably 0 to 2; R is a nonhydrolizable organic group (alkyl, aromatic, organofunctional, or a combination thereof); and X is hydroxy, alkoxy, preferably methoxy or ethoxy, halogen, preferably Cl, Br, or I, acetoxy, acyl or substituted acyl, or a hydrolyzable polymer or other moiety prone to hydrolysis and/or environmentally harmful.

The organosilanes used in the practice of the present invention need not be, and often are not, water soluble. By varying the stabilizer and preparation method, the organosilanes selected for use in the present invention are solubilized in water by the stabilizer.

Numerous art-known organosilanes are suitable for the present stabilization procedures to produce water-stabilized compounds, products and compositions. U.S. Pat. Nos. 5,411,585; 5,064,613; 5,145,592, and the publication entitled "A Guide to DC Silane Coupling Agent" (Dow Corning, 1990) disclose many suitable organosilanes. The contents of these references are hereby incorporated in their entirety herein by this reference for the teachings of suitable organosilanes. These organosilanes are suitable for the formation of the water-stabilized organosilane compounds, products and compositions of the present invention.

Preferred silanes for use in the compounds, products and compositions and methods of the present invention include silanes of the following formulae:

$$(R_1)_3SiR_2N^+(R_3)(R_4)(R_5)Y^-$$

or $$(R_1)_3SiR_2N^+C_5H_5Y^-$$

wherein each $R_1$ is, independently, halogen [Cl, Br, I, F] or $R_6O$, where $R_6$ is H, alkyl of from 1 to about 6 carbon atoms, unsubstituted or substituted, preferably from 1 to about 2 carbon atoms and more preferably 1 carbon atom, or acetyl- or other acyl, including substituted acyl, or $R_6O$ can be derived from any hydroxylated polymer, hydroxylated liquid, or hydroxylated solid regardless of water solubility, or $R_6O$ can be derived from any polyether such as, but not limited to, polyethyleneglycols or polypropyleneglycols, such as poly(propyleneglycol)triol (glycerol propoxylate); $R_2$ is unsubstituted or substituted benzyl- or an unsubstituted or substituted alkyl of from 1 to about 3 carbons atoms, preferably alkyl of from 1 to 3 carbon atoms; $R_3$ and $R_4$ are, independently, lower alkoxy of from 1 to 4 carbon atoms, preferably of 2 carbon atoms, such as $CH_2CH_2OH$, $CH_2CH(OH)CH_3$, alkyl of from 1 to about 22 carbon atoms, preferably from 1 to about 10 carbons atoms and most preferably from 1 to 2 carbon atoms or $R_3$ and $R_4$ can, together, form a morpholine or other cyclic or heterocyclic, unsaturated or saturated, five to seven-membered ring of the formula:

$$-R_3-(R_7)_k-R_4-$$

where k is an integer from 0 to 2 and $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), and $R_7$, where the ring is unsaturated is, N, $N^+H$, $N^+$(alkyl), $N^+$(aryl), $N^+$(benzyl), N—$CH_2$—N, $N^+H$—$CH_2$—N, $N^+$(alkyl)—$CH_2$—N, $N^+$(aryl)—$CH_2$—N, or $N^+$(benzyl)—$CH_2$—N where $R_8$, $R_9$, and $R_{10}$ are, independently, benzyl, polyether, lower alkyl alcohol of from 1 to 4 carbon atoms, lower alkoxy of from 1 to 4 carbon atoms, or alkyl of from 1 to about 22 carbon atoms, preferably 1 to about 10 carbon atoms; $R_5$ is $CH_2C_6H_5$, $CH_2CH_2OH$, $CH_2CH(OH)CH_3$, a polyether such as polyethyleneglycol: —$(CH_2CH_2O)_aH$, polypropyleneglycol: —$(CH_2CH(CH_3)O)_aH$, or alkylated polyoxyethylene: —$(CH_2CH_2O)_aB$ where B is alkyl of from 1 to 22 carbon atoms, unsubstituted or substituted, and where each a is, independently, an integer of from 1 to 12, more preferably of from about 1 to about 5, or $R_5$ is alkyl or perfluoroalkyl of from 1 to about 22 carbon atoms, preferably from about 12 to about 20 carbon atoms and even more preferably from 14 to about 18 carbon atoms; and Y is halogen (such as Cl, Br, I), acetate, sulfate, tosylate or carboxylate, such as acetate, polycarboxylate salts, functionalized carboxylate, such as trifluoroacetate and perfluoroalkylcarboxylates, or other alkyl and arylsulfonate salts, including trifluoromethylsulfonate and perfluoroalkylsulfonate salts, phosphate and phosphonate salts, borate and boronate salts or any other suitable anionic moiety.

Preferred organosilanes include, but are not limited to:
3-(trimethoxysilyl)propyldimethyloctadecyl ammonium chloride,
3-(trimethoxysilyl)propylmethyldi(decyl)ammonium chloride,
3-chloropropyltrimelthylsilane,
octadecyltrimethoxysilane,
perfluorooctyltriethoxysilane,
$(CH_3O)_3Si(CH_2)_3N^+(CH_3)_2C_{18}H_{37}Br^-$,
$(CH_3O)_3Si(CH_2)_3N^+(C_{10}H_{21})CH_3Cl^-$,
$(CH_3O)_3Si(CH_2)_3N^+(C_{10}H_{21})CH_3Br^-$,
$(CH_3O)_3Si(CH_2)_3N^+(CH_3)_3Cl^-$,
$(CH_3O)_3Si(CH_2)_3N^+(CH_3)_2C_8H_{17}Cl^-$,
$(CH_3O)_3Si(CH_2)_3N^+(CH_3)_2C_{10}H_{21}Cl^-$,
$(CH_3O)_3Si(CH_2)_3N^+(CH_3)_2C_{12}H_{25}Cl^-$,
$(CH_3O)_3Si(CH_2)_3N^+(CH_3)_2C_{14}H_{29}Cl^-$,
$(CH_3O)_3Si(CH_2)_3N^+(CH_3)_2C_{16}H_{33}Cl^-$,
$(CH_3O)_3Si(CH_2)_3N^+(CH_3)_2C_{20}H_{41}Cl^-$, $(CH_3O)_3Si(CH_2)_3N^+(C_4H_9)_3Cl^-$,
$(CH_3O)_3Si(CH_2)_3N^+(C_2H_5)_3C^-$,
$(CH_3CH_2O)_3Si(CH_2)_3N^+(CH_3)_2C_{18}H_{27}Cl^-$,
$(CH_3O)_3Si(CH_2)_3NHC(O)(CF_2)_6CF_3$,
$(CH_3O)_3Si(CH_2)_3NHC(O)(CF_2)_{10}(CF_2)_8CF_3$,
$(CH_3O)_3Si(CH_2)_3NHC(O)(CF_2)_{10}CF_3$,
$(CH_3O)_3Si(CH_2)_3NHC(O)(CF_2)_{12}CF_3$,
$(CH_3O)_3Si(CH_2)_3NHC(O)(CF_2)_{14}CF_3$,
$(CH_3O)_3Si(CH_2)_3NHC(O)(CF_2)_{16}CF_3$,
$(CH_3O)_3Si(CH_2)_3NHSO_2(CF_2)_7CF_3$,
$(CH_3O)_3Si(CH_2)_3N^+(CH_3)_2(CH_2)_3NHC(O)(CH_2)_6CH_3$,
$(CH_3O)_3Si(CH_2)_3N^+(CH_3)_2(CH_2)_3NHC(O)(CH_2)_8CH_3$,
$(CH_3O)_3Si(CH_2)_3N^+(CH_3)_2(CH_2)_3NHC(O)(CH_2)_{10}CH_3$,
$(CH_3O)_3Si(CH_2)_3N^+(CH_3)_2(CH_2)_3NHC(O)(CH_2)_{12}CH_3$,
$(CH_3O)_3Si(CH_2)_3N^+(CH_3)_2(CH_2)_3NHC(O)(CH_2)_{14}CH_3$,
$(CH_3O)_3Si(CH_2)_3N^+(CH_3)_2(CH_2)_3NHC(O)(CH_2)_{16}CH_3$,
$(CH_3O)_3Si(CH_2)_3N^+(CH_3)_2(CH_2)_3NHC(O)(CF_2)_6CF_3$,
$(CH_3O)_3Si(CH_2)_3N^+(CH_3)_2(CH_2)_3NHC(O)(CF_2)_8CF_3$,
$(CH_3O)_3Si(CH_2)_3N^+(CH_3)_2(CH_2)_3NHC(O)(CF_2)_{10}CF_3$,
$(CH_3O)_3Si(CH_2)_3N^+(CH_3)_2(CH_2)_3NHC(O)(CF_2)_{12}CF_3$,
$(CH_3O)_3Si(CH_2)_3N^+(CH_3)_2(CH_2)_3NHC(O)(CF_2)_{14}CF_3$,
$(CH_3O)_3Si(CH_2)_3N^+(CH_3)_2(CH_2)_3NHC(O)(CF_2)_{16}CF_3$,
$(CH_3O)_3Si(CH_2)_3N^+(CH_3)_2(CH_2)_3NHSO_2(CF_2)_7CF_3$,
$(CH_3O)_3Si(CH_2)_3N^+(CH_3)_2(CH_2)_3NHSO_2(CF_2)_9CF_3$,
$(CH_3O)_3Si(CH_2)_3N^+(CH_3)_2(CH_2)_3NHSO_2(CF_2)_{11}CF_3$,
$(CH_3O)_3Si(CH_2)_3N^+(CH_3)_2(CH_2)_3NHSO_2(CF_2)_{13}CF_3$,
$(CH_3O)_3Si(CH_2)_3N^+(CH_3)_2(CH_2)_3NHSO_2(CF_2)_{15}CF_3$,
$(CH_3O)_3Si(CH_2)_3N^+(CH_3)_2(CH_2)_3NHSO_2(CF_2)_{16}CF_3$,
aminoethylaminopropyltrimethoxysilane: $NH_2(CH_2)_2NH(CH_2)_3Si(OCH_3)_3$,
3-aminopropyltrimethoxysilane: $NH_2(CH_2)_3Si(OCH_3)_3$,
3-aminopropyltriethoxysilane: $NH_2(CH_2)_3Si(OCH_2CH_3)_3$,
3-chloropropyltrimethoxysilane: $Cl(CH_2)_3Si(OCH_3)_3$,
3-chloropropyltriethoxysilane: $Cl(CH_2)_3Si(OCH_2CH_3)_3$,
3-chloropropyltrichlorosilane: $Cl(CH_2)_3SiCl_3$,
3-glycidoxypropyltrimethoxysilane: $C_3H_5O_2(CH_2)_3Si(OCH_3)_3$,
3-glycidoxypropyltriethoxysilane: $C_3H_5O_2(CH_2)_3Si(OCH_2CH_3)_3$,
3-methacryloxypropyltrimethoxysilane: $C_4H_5O_2(CH_2)_3Si(OCH_3)_3$,
3-methacryloxypropyltriethoxysilane: $C_4H_5O_2(CH_2)_3Si(OCH_2CH_3)_3$, methyldichlorosilane: $CH_3SiHCl_2$,
silane-modified melamine: Dow Corning Q1-6106,
sodium (trihydroxysilyl)propylmethylphosphonate: $NaO(CH_3)P(O)(CH_2)_3Si(OH)_3$, trichlorosilane, $SiHCl_3$,
n-2-vinylbenzylamino-ethyl-3-aminopropyltrimethoxysilane HCL: Dow Corning Z-6032,
vinyltriacetoxysilane: $H_2C=CHSi(OCOCH_3)_3$,
vinyltrimethoxysilane: $H_2C=CHSi(OCH_3)_3$,
vinyltriethoxysilane: $H_2C=CHSi(OCH_2CH_3)_3$,
vinyltrichlorosilane: $H_2C=CHSiCl_3$,
dimethyldichlorosilane: $(CH_3)_2SiCl_2$,
dimethyldimethoxysilane: $(CH_3)_2)_2Si(OCH_3)_2$,
diphenyldichlorosilane: $(CH_6H_5)_2SiCl_2$,
ethyltrichlorosilane: $(C_2H_5)SiCl_3$,
ethyltrimethoxysilane:: $(C_2H_5)Si(OCH_3)_3$,
ethyltriethoxysilane: $(C_2H_5)Si(OCH_2CH_3)_3$,
isobutyltrimethoxysilane,
n-octyltriethoxysilane,
methylphenyldichlorosilane: $CH_3(C_6H_5)SiCl_2$,
methyltrichlorosilane: $CH_3SiCl_3$,
methyltrimethoxysilane: $CH_3Si(OCH_3)_3$,
phenyltrichlorosilane: $C_6H_5SiCl_3$,
phenyltrimethoxysilane: $C_6H_5Si(OCH_3)_3$,
n-propyltrichlorosilane: $C_3H_7SiCl_3$,
n-propyltrimethoxysilane: $C_3H_7Si(OCH_3)_3$,
silicon tetrachloride: $SiCl_4$,
$ClCH_2C_6H_4CH_2CH_2SiCl_{3n}$,
$ClCH_2C_6H_4CH_2CH_2Si(OCH_3)_3$,
$ClCH_2C_6H_4CH_2CH_2Si(OCH_2CH_3)_3$, decyltrichlorosilane,
dichloromethyl(4-methylphenethyl)silane,
diethoxymethylphenylsilane,
[3-(diethylamino)propyl]trimethoxysilane,
3-(dimethoxymethylsilyl)-1-propanethiol,
dimethoxymethylvinylsilane,
3-[tris(trimethylsilyloxy)silyl]propyl methacrylate,
trichloro[4-(chloromethyl)phenyl]silane,
methylbis(trimethylsilyloxy) vinylsilane,
methyltripropoxysilane, and
trichlorocyclopentylsilane.

Stabilizers

As described herein, preferred stabilizers of the present invention preferably contain at least three hydroxy groups, where any two of the three hydroxy groups are preferably separated by at least three intervening atoms, i.e., (HO—A—B—C—OH). Such stabilizers can stabilize aqueous solutions of the above-described organosilanes $R_nSiX_{4-n}$ and are generally useful for stabilization of all such solutions where n is an integer from 0 to 2 and where water solubility or minimization or prevention of water-induced, silanol self-condensation (and associated polymerization) is desired. In particular, preferred stabilizers are polyols containing three or more OH groups and having at least three carbon atoms separating any two OH groups.

In a further embodiment, suitable stabilizers of the present invention are of the formula:

$$[R_{11}(W)_p](R_{33})C[(CH_2)_qOH]_o$$

wherein o is an integer of from 2 to 3; q is an integer greater than 0, preferably 1 or 2; p is an integer from 0 to 1; W is alkyl, polyether, aryl or heteroaryl; $R_{11}$ and $R_{33}$ are, independently, halogen [Cl, Br, I, F], H, $CH_2OH$, $N(CH_2CH_2OH)_2CH_3^+V^-$, hydrocarbon, a heteroatom, or any other suitable functionalized substituent such that the final formulation is soluble in water. Therefore, suitable $R_{11}$ or $R_{33}$ moieties include, but are not limited to, $NH_2$, $NO_2$, $N(H)(CH_2)_3OSO_3H$, $N^+(CH_3)_2(CH_2)_3SO_3^-$, $N(CH_3)_3^+Cl^-$, $(CH_2)OPO_3H_2$, $(CH_2)PO_3H_2$, ZO (where Z is H, alkyl, organofunctional alkyl, aryl, organofunctional aryl, or heteroaryl), ZS(O)r (where Z is H, Na, or any other mono- or di-valent cation including ammonium, alkyl, organofunctional alkyl, aryl, organofunctional aryl, or heteroaryl and r is an integer from 0 to 2), $Z_1Z_2N$ (where $Z_1$ and $Z_2$ are, independently, H, alkyl, organofunctional alkyl, aryl, organofunctional aryl, or heteroaryl), $Z_3Z_4Z_5N^+X^-$ (where $Z_3$, $Z_4$, and $Z_5$ are, independently, alkyl, organofunctional alkyl, aryl, organofunctional aryl, or heteroaryl), $Z_6PO_3$ (where $Z_6$ is H, Na, or any other mono- or di-valent cation including ammonium, alkyl, organofunctional alkyl, aryl, organofunctional aryl, or heteroaryl), and $N(H)R_{34}(CF_2)_eCF_3$ where $R_{34}$ is CO or $SO_2$ and e is an integer of from 1 to 22; and V is halogen [F, Cl, Br, or I], sulfate, tosylate or carboxylate, such as acetate, polycarboxylate salts, functionalized carboxylate, such as trifluoroacetate and perfluoroalkylcarboxylates, or other alkyl and arylsulfonate salts including trifluoromelthylsulfonate and perfluoroalkylsulfonate salts, phosphate and phosphonate salts, borate and boronate salts, or any other suitable negatively charged ion.

In an further embodiment, stabilizers useful for practicing the present invention are of the general formula:

$$(HOCH_2)_2C(R_{12})(R_{13})$$

wherein $R_{12}$ and $R_{13}$ are, independently, H, OH, alkyl of from 1 to about 4 carbon atoms, unsubstituted or substituted with OH, carboxylate, or phosphate esters, such as, but not limited to, $CH_2CO_2^-$, $CH_2OPO_3^-$, $CH_2CH_2OH$, $CH_2CH_2OPO_3^-$. Moreover, $R_{12}$ and $R_{13}$ may also be N, unsubstituted (amino, i.e., $NH_2$) or substituted with O (nitro, i.e., $NO_2$) or substituted to produce an amide, sulfonamide, phosphonamide, oxime, thionamide, quaternary ammonium, imine, imide (such as succinimide), guanidine, amine oxide (such as $N(O)R_{50}R_{51}$, where $R_{50}$ and $R_{51}$ are, independently, lower alkyl alcohol of from 1 to 4 carbon atoms, lower alkoxy of from 1 to 4 carbon atoms, or alkyl of from 1 to about 4 carbon atoms. Where $R_{12}$ or $R_{13}$ is N, preferable stabilizers may be of the following formulae:

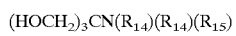

or

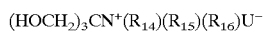

where $R_{14}$ and $R_{15}$ are, independently, H, —O— (i.e., nitro functionality) or alkyl of from 1 to about 4 carbon atoms, unsubstituted or substituted with OH, or piperazine, piperazine derivatives, morpholine, polyalkylether, or benzyl; $R_{16}$ is H, phenyl or alkyl of from 1 to 22 carbons, unsubstituted or substituted with OH, phenyl- or can be polyalkylether, such as polyethylene glycol; and U is halogen [F, Cl, Br, or I], sulfate, tosylate or carboxylate, such as acetate, polycarboxylate salts, functionalized carboxylate, such as trifluoroacetate and perfluoroalkylcarboxylates, or other alkyl and arylsulfonate salts including trifluoromethylsulfonate and perfluoroalkylsulfonate salts, phosphate and phosphonate salts, borate and boronate salts, or any other suitable negatively charged ion.

Not wishing to be bound by theory, it is believed that stabilizers suitable for the present invention preferably require O atoms (usually from hydroxy groups) to be separated by at least three carbons because of favored formation of 6-membered rings consisting of —O—Si—O— from the organosilane and the three atoms (usually carbon) from the stabilizer. With organosilanes of the formula $R_nSiX_{4-n}$, where n is 0 or 1, up to two of the six-membered rings can be generated at any particular silicon atom. With organosilanes of the formula $R_nSiX_{4-n}$, where n is 2, only one 6-membered ring can form. For example, see Scheme 3.

It is believed that effective polyol stabilizers for organosilanes of the formula $RSiX_3$ can generate up to two 6-membered rings for each available silicon atom. But the existence of one or two of the described rings on a particular silicon atom is not critical to the operability of the products, compounds, products and compositions and methods of the present invention, and is instead offered for explication of the believed mechanism by which the present invention operates. With this in mind, not wishing to be bound by theory, it is possible that one or more of the following structures or equilibrations leads to the surprising stabilized organosilanes of the present invention:

1. In water, the stabilizers produce organosilanes, $RSiX_3$, possessing two of the indicated 6-membered rings:

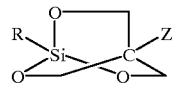

2. In water, the stabilizers produce an equilibrating mixture of organosilanes, $RSiX_3$, existing predominantly as the species possessing one of the indicated 6-membered rings, but in equilibrium with a species possessing two of the indicated 6-membered rings:

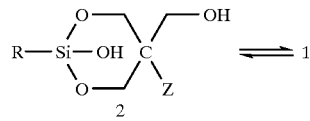

3. In water, the stabilizers produce an equilibrating mixture of organosilanes, $RSiX_3$, existing predominantly as the species possessing none of the 6-membered rings, but in equilibrium with the species possessing one of the indicated 6-membered rings and the species possessing two of the indicated 6-membered rings:

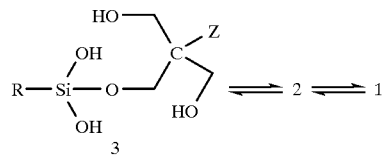

4. In water, the stabilizers are not covalently attached to the organosilane, $RSiX_3$, but associate with the silanetriol through hydrogen-bonding stabilizing it from self-condensation.

5. In water, the stabilizers form linear and/or cyclic oligomers (linear shown below) consisting of regular repeating units of $RSi(OH)_3$ condensed with $(HOCH_2)_3CZ$ units, wherein stabilization is achieved by preventing formation of O—Si—O—Si—O—Si—O polymers and, concurrently, retaining water solubility. Even in this scenario, the formation of a small equilibrium of the 6-membered ring compounds may be important to the stabilization mechanism:

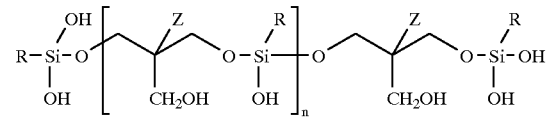

6. In water, the stabilizers form linear and/or cyclic oligomers (linear shown below) consisting of both regular repeating units of $RSi(OH)_3$ condensed with $(HOCH_2)_3CZ$ units and sections containing some short O—Si—O—i—O—Si—O polymeric units, wherein stabilization is achieved by preventing formation of extensive O—Si—O—Si—O—Si—O polymers (linear and/or cyclic) and, concurrently, retaining water solubility. Even in this scenario, the formation of a small equilibrium of the 6-membered ring compounds may be important to the stabilization mechanism:

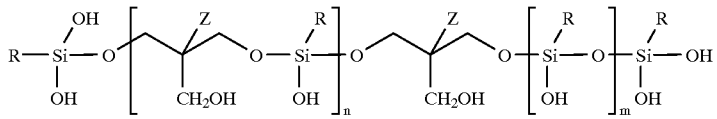

Not wishing to be bound by theory, Scheme 3 shows the reaction scheme for preparing 3-(trimethoxysilyl)propyl-dimethyloctadecyl ammonium chloride, and subsequent hydrolysis and conversion to the fully-complexed pentaerythritol-stabilized form as discussed throughout this specification. This Scheme assumes initial water hydrolysis of the 3-(trimethoxysilyl)propyl-dimethyloctadecyl ammonium chloride, but it is understood that formulation of the stabilized form can also occur directly from the trimethoxy species by alcoholysis:

Moreover, in another embodiment, it is believed that poly(tetrahydrofuran), poly(vinyl)alcohol, hydroxyethyl cellulose, starch and cellulosic derivatives also possess water solubilizing and/or stabilizing utility.

In addition, in a preferable embodiment, when the stabilizer is tris(hydroxymethyl)methanetrimethylammonium iodide, several stabilized organosilanes can be prepared as stable, water-soluble powders by reacting the starting organosilane with the stabilizer in an inert organic solvent and distilling off the methanol that is formed to produce the

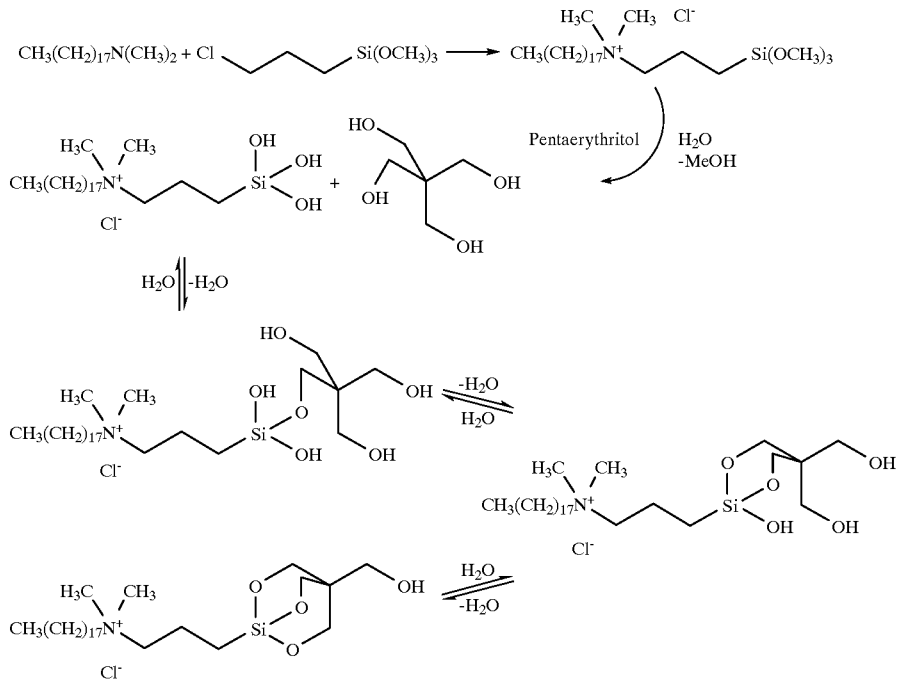

In addition, the viscosity of the water-stabilized quaternary ammonium silane may be varied as follows. When the quaternary ammonium silane is prepared in a solvent such as methanol, the resultant pentaerythritol-stabilized aqueous solution undergoes slight gelling leading to a viscous solution after aging. The binding properties of the organosilane are retained in the viscous product. When prepared as described in Example I without solvent, the solutions are non-viscous after several months, even at the same pH.

Therefore, preferred examples of stabilizers include, but are not limited to: polyols such as pentaerythritol and its higher homologues, i.e., dipentaerythritol, tripentaerythritol, tetrapentaerythritol, etc., tris(hydroxymethyl)ethane, tris(hydroxymethyl)propane, tris(hydroxymethyl)aminomethane, tris(hydroxymethyl)methanetrimethylammonium iodide, and tris(hydroxymethyl)nitromethane.

A further preferred stabilizer is tetrakis(hydroxymethyl) phosphonium chloride [$(HOCH_2)_4P^+Cl^-$].

corresponding trioxasilabicyclooctyl compound (see Formula 1 below) as a stable, water-soluble powder.

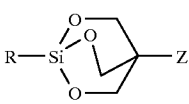

(1)

Such products are useful for convenience of storage and transportation and for blending with water immiscible media such as plasticizers and plastics, clays, mortar, fillers, dyes and pigments. Moreover, such compositions could readily be delivered in an encapsulated or microencapsulated form, wherein the organosilane is regenerated by abrasion or erosion of the capsule thereby providing a continuous, intermittent, or otherwise predetermined supply of the organosilane.

Furthermore, while the preferred pentaerythritol-modified compound is not particularly soluble in solvents other than water, the tris(hydroxymethyl)ethane-stabilized compound is soluble in methanol and probably other solvents. Therefore, that stabilizer could be used to prepare a concentrated, stabilized antimicrobial organosilane which is then diluted for use on-site. Moreover, this stabilizer could also, alternatively, be used to prepare a solid, stabilized antimicrobial organosilane for use by on-site addition of water. Such a concentrated or solid preparations would provide for significant savings cost in shipping and storage of the product. Moreover, the shelf-life of a methanol solution of the tris(hydroxymethyl)ethane stabilized compound is expected to be indefinite.

In a further embodiment, the present invention uses the organosilane-derived antimicrobial 3-(trimethoxysilyl)propyl-dimethyloctadecyl ammonium chloride, but exchanges up to three of the methoxy groups on the silane with a water-soluble stabilizer moiety. Moreover, any remaining methoxy groups on the silane are lost to hydrolysis. Suitable water-soluble stabilizers moieties include polyols, such as but not limited to, tetraols, such as pentaerythritol or its higher homologues (dimers, trimers, etc.), or chemically related variants of pentaerythritol.

pH Stability

In addition, the stabilizing compounds and methods of the present invention are useful for stabilizing organosilanes of the above-described general formula $R_nSiX_{4-n}$ in water under either low or high pH conditions. High pH stabilization occurs through the use of an excess (greater than one molar equivalent) of the stabilizer, or through the use of the stabilizers of the present invention in conjunction with other stabilizers already known to provide some enhancement of stability in water at various pH ranges. See, e.g., U.S. Pat. No. 5,411,585 (which is herein incorporated by this reference), which discloses certain stabilizers. In particular, high pH stability could be achieved through any one of three methods. First, the use of excess (preferably 2.0 to 5.0, or more, molar equivalents) of stabilizer. Second, the use of 0.25 to 5.0 molar equivalents of stabilizer along with the procedures of U.S. Pat. No. 5,411,585. Third, the use of polyol stabilizers, such as $(HOCH_2)_3C(CH_2)_nR_{17}$(where n is an integer from 0 to 4), $(HOCH_2)_3C(aryl)R_{17}$, or $(HOCH_2)_3C(benzyl)R_{17}$ that are chemically modified to possess organofunctional groups $R_{17}$, where $R_{17}$ is any anionic or ionizable functional group that will prevent, inhibit, or retard the polymerization of the silanetriol at high pH. Preferable functional groups $R_{17}$ include, but are not limited to, COOH, COONa, $—P(O)(OH)_2$, $—P(O)(ONa)_2$, $—P(O)(OH)(OR_{18})$, $—P(O)(ONa)(OR_{18})$, $—SO_3H$, $—SO_3Na$, $—B(OH)_2$, $—B(OH)(ONa)$, or $—B(ONa)_2$ where $R_{18}$ is alkyl or perfluoroalkyl, branched or unbranched, of from 1 to 22 carbon atoms, aryl or heteroaryl, such as phenyl or benzyl, polyether, such as a polyethylene glycol or polypropylene glycol. Moreover, in any of these preferred functional groups, it will be readily understood by one of ordinary skill in the art that any hydrogen of a selected hydroxy groups could be replaced with any other suitable mono-valent or di-valent cation, such as, but certainly not limited to, $Na^+$, $K^+$, $NH_4^+$, $Mg^{2+}$, $Ca^{2+}$, or $N(R_{70})_4^+$ where $R_{70}$ is alkyl or perfluoroalkyl, branched or unbranched, of from 1 to 22 carbon atoms, aryl or heteroaryl, such as phenyl or benzyl, polyether, such as a polyethylene glycol or polypropylene glycol.

Uses

The compounds, products and compositions of the present invention are useful for a multitude of purposes. Such purposes include any known use for the starting material organosilanes of the above-described general formula, such as, but not limited to, antimicrobial, water repellant, chemical reaction intermediate, etc. In preferred embodiments, the presently described, water-stabilized, organosilane compounds, products and compositions are suitable to applications such as: 1) treatment of surfaces, including fillers and pigments, 2) additives to coatings such as dyes, or 3) as additives to organic monomers (such as acrylics) prior to formation of the respective polymer.

Therefore, in addition to the utility of prior organosilane quaternary ammonium compounds such as 3-(trimethoxysilyl)propyl-dimethyloctadecyl ammonium chloride as surface bonding antimicrobial agents, numerous other uses of organofunctional silanes are contemplated, such as the use of the compounds, products and compositions of the invention in coating applications which include the treatment of surfaces or particles (pigments or fillers), in primers, in paints, inks, dyes and adhesives, and as reactive intermediates for silicone resin synthesis.

The present invention can be used to prepare, inter alia, agricultural products, cleaning compositions, antimicrobial sponges, antimicrobial bleaching agents, antimicrobial fillers for paints, plastics, or concrete, and to treat concrete structures such as livestock shelters, where microbial infestation is a problem.

In various embodiments, surfaces and substrates treatable with the compounds, products and compositions of the invention solution include, but are not limited to, textiles, carpet, carpet backing, upholstery, clothing, sponges, plastics, metals, surgical dressings, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, water purification systems, and soil. Furthermore, articles treatable with the compounds, products and compositions of the invention include, but are not limited to, air filters and materials used for the manufacture thereof, aquarium filters, buffer pads, fiberfill for upholstery, fiberglass ductboard, underwear and outerwear apparel, polyurethane and polyethylene foam, sand bags, tarpaulins, sails, ropes, shoes, socks, towels, disposal wipes, hosiery and intimate apparel, cosmetics, lotions, creams, ointments, disinfectant sanitizers, wood preservatives, plastics, adhesives, paints, pulp, paper, cooling water, and laundry additives and non-food or food contacting surfaces in general.

For the above described substrates, mixtures and applications, treatment generally involves contacting the article to be treated with a water-stabilized organosilane solution of the present invention, comprising the organosilane-stabilizer derived compound in an aqueous solution, for a period of time sufficient for permanent bonding of the active organosilane ingredient (or portion thereof) to the article. Generally, treatment begins almost immediately upon contact, but preferably requires from about 15 seconds to about 48 hours, more preferably from about 1 minute to about 24 hours, even more preferably from about five minutes to 1 hour, and even more preferably for about 30 minutes. Further general guidelines for application are as follows: For dipping a large object, it is preferred that 1–2 minutes of submersion is allowed in the solution and then the object is permitted to dry or is dried. However, some objects will benefit from very short dipping or contacting times, for example, fabric may pass through an aqueous bath of the composition at a rate of up to 40 yards per minute or more. After dipping, excess solution may be gently wiped or rinsed off. Alternatively, the solution may be sprayed on the substrate. Moreover, the composition of the invention may be placed in a high intensity solid mixer and formed into a powder which is then dried. The dried powder may then be used in a sprayer, if desired. In addition, the solutions may be wiped onto the substrate and applied using sponges or cloths, etc. Moreover, the solutions of the present invention can be added to pigments and fillers and stirred therewith for several (2–3) minutes. In addition, the solutions can be added to an emulsion or other existing formulation prior to use. Also, the solutions can be used in addition to, with or as a spray coolant for extruded fibers. However, one of ordinary skill in the art would recognize that numerous other uses and modes of application are readily apparent from the stabilized organosilane compounds, products and compositions of the present invention and would, without undue experimentation, be able to determine effective application methods and treating times for any particular substrate, article, or other application. In addition, the compositions can be used in padding processes as are known in textile mills.

Moreover, after treating a surface or fabric with the compound, product or composition of the present invention, the surface or fabric may, optionally, be heated to further complete bonding of the compound, product, or composition to the surface or substrate.

The water-stable organosilane compounds, products and compositions of the present invention are, therefore, advantageous in treating a variety of substrates without the use of toxic organic solvents, and provide for the safe, long-term storage of activated organosilanol compound which can be used without further preparation. Moreover, the stabilization scheme described herein does not interfere with the binding of the organosilane (or at least the core, operative portion thereof) to the substrate. In addition, the present invention provides a generally applicable scheme for solvating some water insoluble organosilanes.

Also apparent will be those applications where organosilanes $R_nSiX_{4-n}$ are prepared, dissolved, stored, applied, and in any way used in water. In addition, also apparent will be those applications of organosilanes $R_nSiX_{4-n}$, in other solvents or mixed in other media (solids, polymer mixes, fillers, pigments, powders, dyes or emulsions) where exposure to water occurs but could be detrimental due to undesired or untimely self-condensation of the silanol.

Moreover, the stabilizing compounds and methods could be used in addition to or in conjunction with various art-known stabilization methods for organosilanes, such as the use of ionic or non-ionic surfactants and detergents.

In addition, it is believed that the compounds, products and compositions of the present invention lead to improved wetting and/or coating because the partially hydrolyzed stabilizer/organosilane complex is dense in hydroxyl groups, thus providing for increased hydrogen-bonding to surface OH groups.

Moreover, the present compounds, products and compositions can be used in the incorporation of an organosilane antimicrobial agent in most textile goods (woven and nonwoven) and yarns (synthetic and natural). The process provides articles that are durable and the process itself is effective and does not require additional manufacturing steps or increase manufacturing cost.

Incorporating the compounds, products and compositions of the present invention during the dye process yields a textile material with a built-in antimicrobial agent with the organosilane characteristics, binding and antimicrobial protection. The incorporation process 1) does not add any additional step in the manufacturing process and does not require any equipment modification; and 2) is believed not to lose its antimicrobial characteristics and its effectiveness during further production of the textile goods. By incorporating the water-stable compounds, products and compositions of the present invention during the dye process, not only would the organosilane antimicrobial agent remain unaffected by the dying agent, but the end-product textile goods would also exhibit excellent dyeing properties.

The water-stabilized organosilane compounds, products and compositions of the present invention are useful for a number of applications where the previous instability, insolubility prevented or, at least, hindered or restricted use of some organosilane agents. For example:

Treating food crops (e.g., perishables such as vegetables, fruits, or grains) after removal (picked/harvested) with the compounds, products and compositions of the present invention imparts antimicrobial protection to the outer surface of the food crop. It is believed that such protection occurs without diffusing, migrating or leaching the antimicrobial agent from the bonded antimicrobial coating of the food item, and provides prolonged, safe and non-toxic antimicrobial protection. The method involves treating fruits and vegetables in the rinse cycle, during or after the normal cleaning/water spraying or during or after blanching. Thorough cleaning of fruits and vegetables at the processing plant is preferred for initially removing microorganisms. As one of ordinary skill in the art would recognize, machines are used initially to remove soil, chemicals used in growing, spoilage bacteria, and other foreign materials. These machines also use high velocity water sprays to clean the products. After the cleaning, raw foods or other crop materials are prepared for further processing such blanching (i.e., the food is immersed in water at 190 to 210 degrees F. or exposed to steam).

Microorganisms are controlled by the production plant up until the fruit or vegetable is removed. But once it is removed, organisms such as yeast, mold, and bacteria, begin to multiply, causing the food to loose flavor and change in color and texture. To keep the food from spoiling, a number of methods have been employed, such as refrigerators, to slow down the microorganisms and delay deterioration. Unfortunately, such known methods will preserve raw foods for few weeks at the most. The compounds, products and compositions of the present invention can preserve these items for extended periods. For instance, the compositions, products, or compounds may be added to an existing water line feeding the sprayers for the foods, where such sprayers are used. Otherwise, a simple dipping process may be used, where the dipping requires only a few seconds to impart antimicrobial protection. Low concentrations of 0.1 to 1% aqueous solution (0.1 to 1% by volume) of the compositions provide satisfactory results. In addition, it is believed that the presently described method can also control pathogens on poultry carcasses and in other susceptible meat and fish.

Treating Baby Milk/Juice Bottles, Nipples, Pacifiers and Toys with the compounds, products and compositions of the present invention in the factory or leaching the agent form the bonded surface, can provide prolonged and safe/non-toxic antimicrobial protection. Treating such articles also eliminates odors caused by microbial contamination. A dipping method as described above may be used to treat these articles.

To date, parents have used soaps, detergents, and surface cleaners to alleviate the problems of contamination of these articles. However, these and other similar treatments have, for the most part, been inadequate and required repeated treatment. In addition, these treatments have been found to be limited in their ability to offer broad spectrum control of microorganisms. Therefore, the present compounds, products and compositions can be used to treat these articles to prevent microbial growth and contamination by coating an effective amount of the products and compounds of the invention thereon. The articles employed can be coated by allowing for 1 to 2 minutes submersion (e.g., by dipping), and thereafter, the treated surface is allowed to dry at room temperature. The article is then rinsed of any excess antimicrobial agent. Thorough cleaning and sterilization is a preferred step in removing the microorganisms on the surface of the article prior to "coating" the said articles. In addition, preferably concentrations of 10% or more by volume of the compounds, products and compositions of the invention are used for long lasting protection.

Treating surgical gloves with the compounds, products and compositions of the present invention before or during a surgical procedure can kill microorganisms on contact without. It is believed that the treated gloves do not diffuse or leach the antimicrobial agent from the glove surface and provide prolonged antimicrobial activity with safe and non-toxic antimicrobial protection. Surgical gloves are treated, preferably, by submersing in the solution of Example I, diluted to 1% W/V for at least 30 seconds. This method will permit doctors to use and, if necessary, re-use the same gloves (even without removing them) without undue fear of contamination.

Moreover, one of ordinary skill in the art would be able to implement numerous other end uses based upon the disclosure of the compounds, products and compositions of the present invention. For instance, the following uses, applications and substrates, are contemplated:

1. Concrete and Grout, Concrete Water Conduits, Storm and Sewer Pipes treated with the compounds, products and compositions of the present invention Agents to kill microorganisms on contact and provide prolonged antimicrobial protection to prevent deterioration of the concrete and its coatings
2. Tooth Brushes, Combs, Hair Brushes, Dentures and Retainers
3. Spa and Pool Filters meeting stringent requirements that no other antimicrobial agent can meet and protection for Air Filtration such as air conditioning filters, HVAC applications and cabin air
4. Marble Slabs (building facia, tombs, floors) treated with the compounds, products and compositions of the present invention
5. Rubbing Alcohol
6. Statues and exposed are work
7. HDP, high density polyester fabric plastic covers for dump sites, water reservoirs and generally for soil protection
8. Liquid Additive (as flower water preservative for potted plants and cut flowers)
9. Silicone and Teflon coated Fiberglass with antimicrobial protection including acrylic backing wall covering
10. Dryvitt and Stucco finish
11. Waterproofing treated with the compounds, products and compositions of the present invention
12. A method of treating blended cotton before or after picking machines make the cotton into rolls or laps
13. Food packaging and containers
14. Bio-films and adhesives (tapes and silicone wafers)
15. Single Ply Roofing and Roof shingles
16. Fiberglass reinforcement product, such as, but not limited to, boat hulls, grain and food storage tanks, tubs, and enclosures In a further embodiment, the compound, product, or composition of the present invention can be incorporated into a retail or commercial cleaning product without the necessity to use quaternary amine stabilizers, such as those described in U.S. Pat. No. 5,145,696, the contents of which are hereby incorporated by this reference. Such a cleaning product could be formulated with the following ingredients (by weight %):

| | |
|---|---|
| Water | 86.5% |
| Soda Ash | 2.0% |
| Sodium Metasilicate, Penta | 4.0% |
| Epta (38%) | 1.0% |
| Tetrapotassium pyrophosphate | 1.0% |
| Ammonyx LO | 1.0% |
| Cationic Surfactant | 1.0% |
| Surfonic N-102 | 2.0% |
| The composition of Example I | 1.5% |
| | 100% |

The preferred embodiments of the above-described water-stabilized antimicrobial compounds, products, compositions, and methods are set forth in the following examples. Other features of the invention will become apparent from the following examples, which are for illustrative purposes only and are not intended as a limitation upon the present invention.

EXAMPLE I

In a preferred embodiment, the present invention provides the following water-stable, pentaerythritol-modified silylated quaternary ammonium salt of formula A:

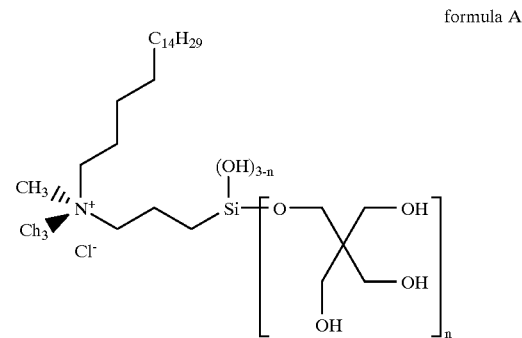

formula A wherein n is an integer from 1 to 3. While the present Example is described with reference to formula A, it is expressly understood that variations in the specified structure are possible. Therefore, the products produced by admixing the silanes of the present invention with the stabilizers of the present invention are also within the scope of the present invention, as claimed. It is believed that the preferred molecule of formula A is a water soluble linear and/or cross-linked oligomer generated by the formation of an equilibrating mixture of intramolecular O—Si—O bonds within the same molecule of formula A and by the formation of intermolecular O—Si—O bonds between different molecules of formula A, as shown in formula B:

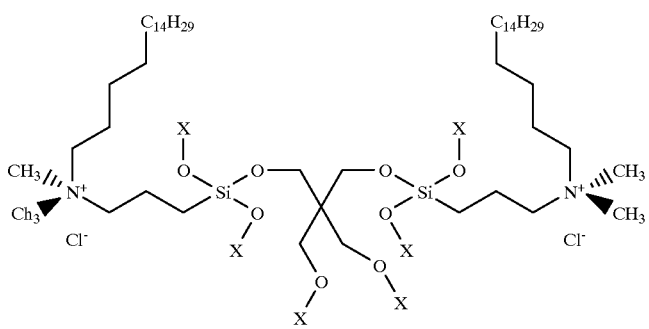

formula B wherein X is, independently, H or intra- or intermolecular linkages to other molecules of formula A. Upon application of the mixture of formulas A and B, the pentaerythritol is most likely partially liberated and the product is hydrolyzed to 3-(trihydroxysilyl)propyldimethyloctadecyl ammonium chloride. However, such liberation is not necessary for the operability of the present invention. Its occurrence or non-occurrence does not detract from the general efficacy of the compounds, products and compositions of the present invention. Instead, the notion that pentaerythritol (or any other of the present stabilizers) is liberated is offered as one possible explanation of the surprising utility and efficacy of the claimed invention. It is not clear that the stabilizer must be liberated when the organosilane bonds to a substrate. Because bonding to the substrate can occur through a combination of ionic, hydrogen or covalent bonds, it is likely that the modified organosilanes of the present invention retain the stabilizer moiety, at least to some degree, even after bonding to the substrate.

In particular, for the present example, a 5% W/V (weight/volume) aqueous solution of 3-(trimethoxysilyl)propyldimethyloctadecyl ammonium chloride was prepared as follows. A 22 L reaction flask was charged with 6250 g. (21.0 Mol.) of dimethyloctadecylamine, 5844 g. (29.4 Mol.) of 3-chloropropyltrimethoxysilane, and 76 g. (0.84 Mol.) of trioxane. The mixture was heated to 140° C. for 12 hours while stirring and is then cooled to 80° C. 2 L of methanol was then added and the mixture is cooled to approximately 40° C. This mixture was then transferred to 171 L of water, into which 4000 g. of pentaerythritol had been previously dissolved. After thorough mixing the pH of the solution was checked. If the pH is above 7.0 (basic) a small amount of HCl is added until the pH is below 7.0. The mixture was then diluted to 209 L with additional water. The resulting solution contained approximately 5% 3-(trimethoxysilyl)propyldimethyloctadecyl ammonium chloride, 0.8% 3-chloropropyltrimethoxysilane, and 1.9% pentaerythritol.

The pentaerythritol stabilized 3-(trimethoxysilyl)propyldimethyloctadecyl ammonium chloride is soluble in water up to concentrations of approximately 15% W/V. One of ordinary skill in the art would recognize that the solubility of other organosilanes may vary and depends upon the specific stabilizer used.

EXAMPLE II

The reaction scheme for tris(hydroxymethyl)ethane (THME) stabilization was identical to Example I, with 3500 g. THME substituted for pentaerythritol.

EXAMPLE III

There may be scenarios where it will be desirable or necessary to pre-form the trioxasilylbicyclooctyl species under anhydrous conditions. This may be necessary where the stabilizer is insoluble in water, or sufficient alcoholysis does not occur in aqueous conditions. For the purposes of this Example, the presently contemplated preferred mode for preparing trioxasilylbicyclooctyl species using 3-chloropropyltrimethoxysilane as the organosilane, and tris (hydroxymethyl)methane as the stabilizer was as follows:

A 500 ml round-bottomed flask was charged with toluene (100 ml), sec-butyl alcohol (5 ml), 3-chloropropyltrimethoxysilane (50 g, 252 mmol), and tris (hydroxymethyl)ethane (36.27 g, 302 mmol). The flask was outfitted with a distillation head and receiver and heated to 110° C. for 14 hours after which the theoretical amount of methanol had collected in the receiving flask. The resulting clear mixture was cooled to room temperature and solvents removed under reduced pressure.

In the above Examples, the pentaerythritol or other polyol can be added to the reaction flask at the beginning, and the methanol produced by the alcoholysis collected by distillation.

EXAMPLE IV

Samples of pentaerythritol-stabilized 3-(trimethoxysilyl)propyldimethyloctadecyl ammonium chloride were stable for at least 6 months when stored at room temperature. Preferably, for maximal stability, the pH of the solution was from about 4.0 to about 6.7. However, even when the pH was below 4.0, the samples were stable for up to one month. Below pH about 2.0, samples were stable for up to one week. Moreover, at pH 7.0 to about 10.2, the samples were also stable for at least one month. Above pH 11.0, however, the samples were unstable and become hazy within minutes. In such cases, the compounds, products and compositions would benefit from the high pH stabilization procedures as described herein. Similar results were found for samples of tris(hydroxymethyl)ethane-stabilized 3-(trimethoxysilyl)propyldimethyloctadecyl ammonium chloride, which showed stability for at least 6 months when stored at room temperature.

Table 1 summarizes stability data based upon appearance of the preparation after the specified period of time:

TABLE 1

Stability of unstabilized and stabilized 3-(trimethoxysilyl)propyldimethyloctadecyl ammonium chloride

| Stabilizer | Initial pH | 1 wk. | 1 mo. | 2 mo. | 3 mo. | 6 mo. |
|---|---|---|---|---|---|---|
| none | 6.5 | clear | hazy | | | |
| none | 5.7 | clear | hazy | | | |
| none | 2.0 | clear | hazy | | | |
| none | 1.15 | hazy | | | | |
| PE* | 6.5 | clear | clear | clear | ND | ND |
| PE | 5.2 | clear | clear | clear | clear | ND |
| PE | 4.7 | clear | clear | clear | clear | clear |
| THME** | 5.7 | clear | clear | clear | clear | ND |
| PE | 8.5 | clear | ND | | | |
| none | 8.5 | hazy/gel | | | | |
| PE | 9.2 | clear | ND | | | |
| PE | 10.2 | clear | ND | | | |
| PE | 11.1 | hazy | | | | |

ND = no data
*PE = Pentaerythritol
**THME = tris(hydroxymethyl)ethane

EXAMPLE V

Chloropropyl trimethoxysilane, $Cl(CH_2)_3Si(OMe)_3$, is insoluble in water. However, addition of $Cl(CH_2)_3Si(OMe)_3$ to water containing pentaerythritol produced a clear solution after standing overnight. Therefore, water insoluble silanes such as $Cl(CH_2)_3Si(OMe)_3$ can be used in any application where a water solution of a functionalized organosilane finds utility.

EXAMPLE VI

The process was carried out as follows. In a dye bath were mixed the following ingredients: antimicrobial agent, pigment color (dyes), binder, antimigrant, wetter, ammonia. Into this bath, a polyester camper material was immersed. After treatment, the antimicrobial effectiveness of the polyester camper was tested and found to exhibit antimicrobial properties.

In particular, the antimicrobial testing involved the Southern Phenix Textile Fabric 401A Gray, Style 6048 subjected to the Dow Corning "Shake Flask Test". In particular, a full scale run at the factory was performed by Southern Phenix to determine whether the composition of Example I could be incorporated in the dye process. The following steps were followed. A preparatory treatment including scouring of the fabric to remove oils, dirt, lint and any residue of sizing compounds followed by drying to remove excess moisture was undertaken. The fabric was then immersed in a dye bath having the following ingredients, added at room temperature in the order listed to a 500 gal. kettle:

| | | |
|---|---|---|
| 1600 | lbs. | water |
| 2.5 | lbs. | Ammonia |
| 12.5 | lbs. | Wetter EP |
| 100 | lbs. | Acrylic Binder (BF Goodrich Product #26345) |
| 25 | lbs. | Antimigrant C-45 (BF Goodrich) |
| 0.1 | lbs. | Metropad Red #6505 Dye |
| 0.4251 | lbs. | Metropad Blue #6735 Dye |
| 1.084 | lbs. | Metropad Black #6220 Dye |
| 2 | lbs. | Antifoaming Agent (Ashland Chemicals Product # 1398-AS) |
| 193 | lbs. | 5% W/V Composition of Example I (pentaerythritol-stabilized 3-(trimethoxysilyl)propyldimethyloctadecyl ammonium chloride). |

The sample was then treated with this composition by the known padding process at 50 yards/minute. The dye fabric in this example was then dried (as is generally contemplated when dyeing articles) and tested. The results demonstrated that the antimicrobial agent could be incorporated into the fabric during the dye process without affecting either the antimicrobial properties or the dyeing process.

Moreover, the same fabric was tested under the same dye conditions but without the antimicrobial agent. That fabric was finished (dip process) with 2% fluorocarbon (similar to Scotchguard® (3M, Minneapolis, Minn.) and 10% by weight of the fabric and dried at 400° F. at 40 yards per minute. The test results were also satisfactory (i.e., the resulting fabric showed statistically significant ability to reduce pathogens).

EXAMPLE VII

Various articles treated with the pentaerythritol stabilized organosilane composition of Example I were tested for antimicrobial efficacy. In particular, Southern Phenix Textile, Inc., Fabric 410A Gray, Style 6048, Finish ES, Lot 14741 was tested using the 1) Dow Corning "Shake Flask Test" method (0923) and the 2) Kirby Bauer Standard Antimicrobial Susceptibility Test. The articles were prepared by dipping the fabric in a bath of the composition of Example I diluted with water to a 1% W/V concentration, and 10% pick-up/add-on by weight of the fabric was calculated and observed. The fabric was then dried at temperature of 270° F. to remove the water. Optimum application and drying conditions of the material were determined before the solution was made. The treated material was tested using the two different test methods to establish 1) % reduction of the microorganisms the sample was subjected to and 2) no zone inhibition. Results from these two tests were found to be very satisfactory, i.e., a 99.90% reduction of bacterial count and no zone inhibition.

Next, Southern Phenix 5 oz. Camper Material (STD), Napery Style 6662, Drapery/Slipcover/Cubicle Curtain Style 7242, Shoe Liner Style 8428, Mattress Ticking Style 6832-1 was subjected to the above-referenced standardized "Shake Flask" Test. The above fabric was prepared by dipping in a bath of the composition of Example I, diluted with water to 1% W/V concentration, and 10% pick-up/add-on by weight of the fabric was calculated and observed. The fabric was then dried at temperature of 280° F. to remove the water. Optimum application and drying conditions of the material were determined before the solution was made. Again, the fabrics demonstrated significant antimicrobial activity.

Next, Remay Filtration Media 1) Spa, Pool or Hot Tub, Media Style 2040 Filter and 2) Protection Media for Air Filtration. (A/C Filters, HVAC Applications & Cabin Air) were tested for antimicrobial activity using the AATCC4352 0 "Shake Flask Test" and the AATCC 147—1993 "Zone of Inhibition Test". The spunbonded polyester sample filter material was submersed in a solution of the composition of Example I. The sample was allowed to soak for 1–2 minutes, and the treated surface was allowed to dry at air temperature (68–72° F.). The results showed that the treated filter material was prevented from building up any significant amount of microorganisms. These results required no pH adjustment unlike some other filter treatments.

Next, 1) Emory White Linen (STD) Fabric, 2) DCI, Inc. 32 Oz Silicone Coated Fiberglass Fabric, 3) Heywinkel-Polyester Coated Vinyl Fabric, and 4) Ferro Corp.—20 Mil PVC Placques were tested using the Dow Corning "Shake Flask Test". The test compound used in the above articles was the 5% W/V solution of Example I. The samples were submersed (one by one) and allowed to soak for 1 minute. The treated materials were then allowed to dry at room temperature. Emory white linen fabric was also hand washed one and four times and tested as well. The results showed that the treated articles demonstrated significant antimicrobial activity.

Next, a 3M O-Cello Sponge and an EZ>>> ONE Paint Cellulose Sponge were tested using the ATCC-4352 0 "Shake Flask Test" and the ATCC 147—1993 "Zone of Inhibition Test". The test composition used for these tests was the composition of Example I diluted to 1% W/V in water. The EZ>>> ONE Paint Cellulose Sponge was removed from its package and saturated with 400 ml of the composition. The solution was allowed to contact the sponge for ten minutes and then the sponge was wrung out. The sponge was allowed to dry overnight. The 3M sponge was removed from its package and subjected to the same tests as the EZ sponge. The treated EZ sponge (treated with the composition of the invention), demonstrated significant antimicrobial activity and zone of inhibition. The 3M sponge demonstrated antimicrobial activity and zone of inhibition as well. The untreated EZ sponge demonstrated no inhibition and no zone of inhibition.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as is exemplary only, with the true scope and spirit of the invention being indicated by the following claims.

What is claimed is:

1. A water-stable composition comprising water and a product that is formed by reacting in water
   a) an organosilane of the formula $R_nSiX_{4-n}$ where n is an integer of from 0 to 2; each R is, independently, a nonhydrolyzable organic group further wherein each R is, independently, alkyl, alkyl alcohol, or aromatic; and each X is, independently, a hydrolyzable group, further wherein each X is, independently, hydroxy, alkoxy, halogen, acetyl, acetoxy, acyl, a hydroxylated solid or liquid polymeric moiety, polyether or polyalkylether, with
   b) a polyol containing at least three hydroxy groups, wherein all of the hydroxy groups are separated by at least three intervening atoms, wherein the polyol is of the formula I:

$$\{R_{11}(W)_p\}(R_{33})_{3-o}C\{(CH_2)_qOH\}_o \quad (I)$$

wherein
   o is an integer of from 2 to 3;
   q is an integer of from 1 to 2;
   p is an integer of from 0 to 1;
   W is alkyl, polyether, aryl or heteroaryl;
   $R_{11}$ and $R_{33}$ are, independently, halogen, H, $CH_2OH$, $N(CH_2CH_2OH)_2CH_3^+V^-$, $NH_2$, $NO_2$, $N(H)(CH_2)_3OSO_3H$, $N^+(CH_3)_2(CH_2)_3SO_3^-$, $N(CH_3)_3^+V^-$, $(CH_2)OPO_3H_2$, $(CH_2)PO_3H_2$,
   $N(H)R_{34}(CF_2)_eCF_3$ where e is an integer of from 1 to about 22 and $R_{34}$ is CO or $SO_2$,
   $(W)_pZO$ where Z is H, alkyl, aryl, or heteroaryl,
   $(W)_pZS(O)_r$ where Z is H, Na, a suitable mono- or di-valent cation, alkyl, aryl, or heteroaryl and r is an integer from 0 to 2,
   $(W)_pZ_1Z_2N$ where $Z_1$ and $Z_2$ are, independently, H, alkyl, aryl, or heteroaryl,
   $(W)_pZ_3Z_4Z_5N^+Q^-$ where $Z_3$, $Z_4$, and $Z_5$ are, independently, H, alkyl, aryl, or heteroaryl and where $Q^-$ is a suitable anionic moiety to form a salt, or
   $(W)_pZ_6PO_3$ where $Z_6$ is H, Na, a suitable mono- or di-valent cation, alkyl, aryl, or heteroaryl; and
   $V^-$ is a suitable anionic moiety to form the salt of the compound of formula I.

2. The composition of claim 1, wherein $V^-$ is halide, sulfate, tosylate, carboxylate, polycarboxylate, alkyl, arylsulfonate, phosphate, phosphonate, borate, or boronate.

3. The composition of claim 1, wherein W is alkyl of from 1 to 22 carbon atoms.

4. The composition of claim 1, wherein W is alkyl of from 1 to 10 carbon atoms.

5. The composition of claim 1, wherein W is alkyl of from 1 to 3 carbon atoms.

6. The composition of claim 1, wherein W is polyether.

7. The composition of claim 1, wherein W is a polypropyleneglycol.

8. The composition of claim 1, wherein W is a polyethyleneglycol.

9. The composition of claim 1, wherein W is aryl.

10. The composition of claim 1, wherein W is phenyl or benzyl.

11. The composition of claim 1, wherein W is heteroraryl, wherein the one or more heteroatoms are, independently, N, O, or S.

12. The composition of claim 1, wherein the organosilane is 3-(trimethoxysilyl)propyldimethyloctadecyl ammonium chloride, 3-(trimethoxysilyl)propylmethyldi(decyl) ammonium chloride, 3-chloropropyltrimethylsilane, 3-chloropropyltrimethoxysilane, octadecyltrimethoxysilane, or perfluorooctyltriethoxysilane and the polyol is pentaerythritol, dipentaerythritol, tripentaerythritol, tetrapentaerythritol, tris(hydroxymethyl)ethane, tris(hydroxymethyl)propane, tris(hydroxymethyl) nitromethane, tris(hydroxymethyl)aminomethane, or tris (hydroxymethyl)methanetrimethyl ammonium iodide.

13. The composition of claim 1, wherein the organosilane is $(CH_3O)_3Si(CH_2)_3N^+(CH_3)_2C_{18}H_{37}Br^-$, $(CH_3O)_3Si(CH_2)_3$ $N^+(C_{10}H_{21})CH_3Cl^-$, $(CH_3O)_3Si(CH_2)_3N^+(C_{10}H_{21})CH_3Br^-$, $(CH_3O)_3Si(CH_2)_3N^+(CH_3)_3Cl^-$, $(CH_3O)_3Si(CH_2)_3N^+(CH_3)_2C_8H_{17}Cl^-$, $(CH_3O)_3Si(CH_2)_3N^+(CH_3)_2C_{10}H_{21}Cl^-$, $(CH_3O)_3Si(CH_2)_3N^+(CH_3)_2C_{12}H_{25}Cl^-$, $(CH_3O)_3Si(CH_2)_3N^+(CH_3)_2C_{14}H_{29}Cl^-$, $(CH_3O)_3Si(CH_2)_3N^+(CH_3)_2C_{16}H_{33}Cl^-$, $(CH_3O)_3Si(CH_2)_3N^+(CH_3)_2C_{20}H_{41}Cl^-$, $(CH_3O)_3Si(CH_2)_3N^+(C_4H_9)_3Cl^-$, $(CH_3O)_3Si(CH_2)_3N^+(C_2H_5)_3Cl^-$, $(CH_3CH_2O)_3Si(CH_2)_3N^+(CH_3)_2C_{18}H_{27}Cl^-$, $(CH_3O)_3Si(CH_2)_3NHC(O)(CF_2)_6CF_3$, $(CH_3O)_3Si(CH_2)_3NHC(O)(CF_2)_8CF_3$, $(CH_3O)_3Si(CH_2)_3NHC(O)(CF_2)_{10}CF_3$, $(CH_3O)_3Si(CH_2)_3NHC(O)(CF_2)_{12}CF_3$, $(CH_3O)_3Si(CH_2)_3NHC(O)(CF_2)_{14}CF_3$, $(CH_3O)_3Si(CH_2)_3NHC(O)(CF_2)_{16}CF_3$, $(CH_3O)_3Si(CH_2)_3NHSO_2(CF_2)_7CF_3$, $(CH_3O)_3Si(CH_2)_3N^+(CH_3)_2(CH_2)_3NHC(O)(CH_2)_6CH_3$, $(CH_3O)_3Si(CH_2)_3N^+(CH_3)_2(CH_2)_3NHC(O)(CH_2)_8CH_3$, $(CH_3O)_3Si(CH_2)_3N^+(CH_3)_2(CH_2)_3NHC(O)(CH_2)_{10}CH_3$, $(CH_3O)_3Si(CH_2)_3N^+(CH_3)_2(CH_2)_3NHC(O)(CH_2)_{12}CH_3$, $(CH_3O)_3Si(CH_2)_3N^+(CH_3)_2(CH_2)_3NHC(O)(CH_2)_{14}CH_3$, $(CH_3O)_3Si(CH_2)_3N^+(CH_3)_2(CH_2)_3NHC(O)(CH_2)_{16}CH_3$, $(CH_3O)_3Si(CH_2)_3N^+(CH_3)_2(CH_2)_3NHC(O)(CF_2)_6CF_3$, $(CH_3O)_3Si(CH_2)_3N^+(CH_3)_2(CH_2)_3NHC(O)(CF_2)_8CF_3$, $(CH_3O)_3Si(CH_2)_3N^+(CH_3)_2(CH_2)_3NHC(O)(CF_2)_{10}CF_3$, $(CH_3O)_3Si(CH_2)_3N^+(CH_3)_2(CH_2)_3NHC(O)(CF_2)_{12}CF_3$, $(CH_3O)_3Si(CH_2)_3N^+(CH_3)_2(CH_2)_3NHC(O)(CF_2)_{14}CF_3$, $(CH_3O)_3Si(CH_2)_3N^+(CH_3)_2(CH_2)_3NHC(O)(CF_2)_{16}CF_3$, (CH$_3$O)$_3$Si(CH$_2$)$_3$N$^+$(CH$_3$)$_2$(CH$_2$)$_3$NHSO$_2$(CF$_2$)$_7$CF$_3$,
(CH$_3$O)$_3$Si(CH$_2$)$_3$N$^+$(CH$_3$)$_2$(CH$_2$)$_3$NHSO$_2$(CF$_2$)$_9$CF$_3$,
(CH$_3$O)$_3$Si(CH$_2$)$_3$N$^+$(CH$_3$)$_2$(CH$_2$)$_3$NHSO$_2$(CF$_2$)$_{11}$CF$_3$,
(CH$_3$O)$_3$Si(CH$_2$)$_3$N$^+$(CH$_3$)$_2$(CH$_2$)$_3$NHSO$_2$(CF$_2$)$_{13}$CF$_3$,
(CH$_3$O)$_3$Si(CH$_2$)$_3$N$^+$(CH$_3$)$_2$(CH$_2$)$_3$NHSO$_2$(CF$_2$)$_{15}$CF$_3$, or
(CH$_3$O)$_3$Si(CH$_2$)$_3$N$^+$(CH$_3$)$_2$(CH$_2$)$_3$NHSO$_2$(CF$_2$)$_{16}$CF$_3$.

14. The composition of claim 1, wherein the polyol is pentaerythritol, dipentaerythritol, tripentaerythritol, tetrapentaerythritol, tris(hydroxymethyl)ethane, tris(hydroxymethyl)propane, tris(hydroxymethyl)nitromethane, tris(hydroxymethyl)aminomethane, tris(hydroxymethyl)methane trimethyl ammonium iodide, or tetrakis(hydroxymethyl)phosphonium chloride.

15. A method of treating a substrate, comprising contacting the substrate with a sufficient amount of the composition of claim 1 for a period of time sufficient for treatment of the substrate.

16. A treated substrate having adhered thereto the composition of claim 1.

17. The composition of claim 1, wherein the organosilane is NH$_2$(CH$_2$)$_2$NH(CH$_2$)$_3$Si(OCH$_3$)$_3$, NH$_2$(CH$_2$)$_3$Si(OCH$_3$)$_3$, NH$_2$(CH$_2$)$_3$Si(OCH$_2$CH$_3$)$_3$, Cl(CH$_2$)$_3$Si(OCH$_3$)$_3$, Cl(CH$_2$)$_3$Si(OCH$_2$CH$_3$)$_3$, Cl(CH$_2$)$_3$SiCl$_3$, C$_3$H$_5$O$_2$(CH$_2$)$_3$Si(OCH$_3$)$_3$, C$_3$H$_5$O$_2$(CH$_2$)$_3$Si(OCH$_2$CH$_3$)$_3$, C$_4$H$_5$O$_2$(CH$_2$)$_3$Si(OCH$_3$)$_3$, C$_4$H$_5$O$_2$(CH$_2$)$_3$Si(OCH$_2$CH$_3$)$_3$, CH$_3$SiHCl$_2$, NaO(CH$_3$O)P(O)(CH$_2$)$_3$Si(OH)$_3$, SiHCl$_3$, n-2-vinylbenzylamino-ethyl-3-aminopropyltrimethoxysilane HCl, H$_2$C=CHSi(OCOCH$_3$)$_3$, H$_2$C=CHSi(OCH$_3$)$_3$, H$_2$C=CHSi(OCH$_2$CH$_3$)$_3$, H$_2$C=CHSiCl$_3$, (CH$_3$)$_2$SiCl$_2$, (CH$_3$)$_2$Si(OCH$_3$)$_2$, (C$_6$H$_5$)$_2$SiCl$_2$, (C$_2$H$_5$)SiCl$_3$, (C$_2$H$_5$)Si(OCH$_3$)$_3$, (C$_2$H$_5$)Si(OCH$_2$CH$_3$)$_3$, isobutyltrimethoxysilane, n-octyltriethoxysilane, CH$_3$(C$_6$H$_5$)SiCl$_2$, CH$_3$SiCl$_3$, CH$_3$Si(OCH$_3$)$_3$, C$_6$H$_5$SiCl$_3$, C$_6$H$_5$Si(OCH$_3$)$_3$, C$_3$H$_7$SiCl$_3$, C$_3$H$_7$Si(OCH$_3$)$_3$, SiCl$_4$, ClCH$_2$C$_6$H$_4$CH$_2$CH$_2$SiCl$_3$, ClCH$_2$C$_6$H$_4$CH$_2$CH$_2$Si(OCH$_3$)$_3$, ClCH$_2$C$_6$H$_4$CH$_2$CH$_2$Si(OCH$_2$CH$_3$)$_3$, decyltrichlorosilane, dichloromethyl(4-methylphenethyl)silane, diethoxymethylphenylsilane, {3-(diethylamino)propyl}trimethoxysilane, 3-(dimethoxymethylsilyl)-1-propanethiol, dimethoxymethylvinylsilane, 3-{tris(trimethylsilyloxy)silyl}propyl methacrylate, trichloro{4-(chloromethyl)phenyl}silane, methylbis(trimethylsilyloxy)vinylsilane, methyltripropoxysilane, or trichlorocyclopentylsilane.

18. The composition of claim 1, wherein the polyol is of the formula XIV:

$$(HOCH_2)_{aa}C\{CH_2OP(R_{60})(R_{61})\}_{4-aa} \qquad (XIV)$$

or is aryl substituted with from 2 to 6 moieties of —(OCH$_2$)C(CH$_2$OH)$_3$; wherein aa is an integer of from 0 to 4; each R$_{60}$ is, independently, O$_2$ or OH; and each R$_{61}$ is, independently, H, a mono- or di-valent cation, or OR$_{62}$ where R$_{62}$ is alkyl of from 1 to 22 carbon atoms, lower alkyl alcohol of from 1 to 4 carbon atoms, or alkoxy of from 1 to 4 carbon atoms.

19. A water stable composition comprising water and a compound that is formed by reacting in water components comprising
a) an organosilane of the formula R$_n$SiX$_{4-n}$ where n is an integer of from 0 to 3; each R is, independently, a nonhydrolizable organic group; and each X is, independently, a hydrolyzable group, with
b) a polyol containing at least three hydroxy groups, wherein all of the hydroxy groups are separated by at least three intervening atoms,
wherein the polyol is not hydroxyethyl cellulose.

20. The composition of claim 19, wherein the organosilane is (CH$_3$O)$_3$Si(CH$_2$)$_3$N$^+$(CH$_3$)$_2$C$_{18}$H$_{37}$Br$^-$, (CH$_3$O)$_3$Si(CH$_2$)$_3$N$^+$(C$_{10}$H$_{21}$)CH$_3$Cl$^-$, (CH$_3$O)$_3$Si(CH$_2$)$_3$N$^+$(C$_{10}$H$_{21}$)CH$_3$Br$^-$, (CH$_3$O)$_3$Si(CH$_2$)$_3$N$^+$(CH$_3$)$_3$Cl$^-$, (CH$_3$O)$_3$Si(CH$_2$)$_3$N$^+$(CH$_3$)$_2$C$_8$H$_{17}$Cl$^-$, (CH$_3$O)$_3$Si(CH$_2$)$_3$N$^+$(CH$_3$)$_2$C$_{10}$H$_{21}$Cl$^-$, (CH$_3$O)$_3$Si(CH$_2$)$_3$N$^+$(CH$_3$)$_2$C$_{12}$H$_{25}$Cl$^-$, (CH$_3$O)$_3$Si(CH$_2$)$_3$N$^+$(CH$_3$)$_2$C$_{14}$H$_{29}$Cl$^-$, (CH$_3$O)$_3$Si(CH$_2$)$_3$N$^+$(CH$_3$)$_2$C$_{16}$H$_{33}$Cl$^-$, (CH$_3$O)$_3$Si(CH$_2$)$_3$N$^+$(CH$_3$)$_2$C$_{20}$H$_{41}$Cl$^-$, (CH$_3$O)$_3$Si(CH$_2$)$_3$N$^+$(C$_4$H$_9$)$_3$Cl$^-$, (CH$_3$O)$_3$Si(CH$_2$)$_3$N$^+$(C$_2$H$_5$)$_3$Cl$^-$, (CH$_3$CH$_2$O)$_3$Si(CH$_2$)$_3$N$^+$(CH$_3$)$_2$C$_{18}$H$_{27}$Cl$^-$, (CH$_3$O)$_3$Si(CH$_2$)$_3$NHC(O)(CF$_2$)$_6$CF$_3$, (CH$_3$O)$_3$Si(CH$_2$)$_3$ NHC(O)(CF$_2$)$_8$CF$_3$, (CH$_3$O)$_3$Si(CH$_2$)$_3$NHC(O)(CF$_2$)$_{10}$CF$_3$, (CH$_3$O)$_3$Si(CH$_2$)$_3$NHC(O)(CF$_2$)$_{12}$CF$_3$, (CH$_3$O)$_3$Si(CH$_2$)$_3$NHC(O)(CF$_2$)$_{14}$CF$_3$, (CH$_3$O)$_3$Si(CH$_2$)$_3$NHC(O)(CF$_2$)$_{16}$CF$_3$, (CH$_3$O)$_3$Si(CH$_2$)$_3$NHS(O)(CF$_2$)$_7$ CF$_3$,
(CH$_3$O)$_3$Si(CH$_2$)$_3$N$^+$(CH$_3$)$_2$(CH$_2$)$_3$NHC(O)(CH$_2$)$_6$ CH$_3$,
(CH$_3$O)$_3$Si(CH$_2$)$_3$N$^+$(CH$_3$)$_2$(CH$_2$)$_3$NHC(O)(CH$_2$)$_8$ CH$_3$,
(CH$_3$O)$_3$Si(CH$_2$)$_3$N$^+$(CH$_3$)$_2$(CH$_2$)$_3$NHC(O)(CH$_2$)$_{10}$ CH$_3$,
(CH$_3$O)$_3$Si(CH$_2$)$_3$N$^+$(CH$_3$)$_2$(CH$_2$)$_3$NHC(O)(CH$_2$)$_{12}$ CH$_3$,
(CH$_3$O)$_3$Si(CH$_2$)$_3$N$^+$(CH$_3$)$_2$(CH$_2$)$_3$NHC(O)(CH$_2$)$_{14}$ CH$_3$,
(CH$_3$O)$_3$Si(CH$_2$)$_3$N$^+$(CH$_3$)$_2$(CH$_2$)$_3$NHC(O)(CH$_2$)$_{16}$ CH$_3$,
(CH$_3$O)$_3$Si(CH$_2$)$_3$N$^+$(CH$_3$)$_2$(CH$_2$)$_3$NHC(O)(CF$_2$)$_6$ CF$_3$,
(CH$_3$O)$_3$Si(CH$_2$)$_3$N$^+$(CH$_3$)$_2$(CH$_2$)$_3$NHC(O)(CF$_2$)$_8$ CF$_3$,
(CH$_3$O)$_3$Si(CH$_2$)$_3$N$^+$(CH$_3$)$_2$(CH$_2$)$_3$NHC(O)(CF$_2$)$_{10}$ CF$_3$,
(CH$_3$O)$_3$Si(CH$_2$)$_3$N$^+$(CH$_3$)$_2$(CH$_2$)$_3$NHC(O)(CF$_2$)$_{12}$ CF$_3$,
(CH$_3$O)$_3$Si(CH$_2$)$_3$N$^+$(CH$_3$)$_2$(CH$_2$)$_3$NHC(O)(CF$_2$)$_{14}$ CF$_3$,
(CH$_3$O)$_3$Si(CH$_2$)$_3$N$^+$(CH$_3$)$_2$(CH$_2$)$_3$NHC(O)(CF$_2$)$_{16}$CF$_3$,
(CH$_3$O)$_3$Si(CH$_2$)$_3$N$^+$(CH$_3$)$_2$(CH$_2$)$_3$NHSO$_2$(CF$_2$)$_7$ CF$_3$,
(CH$_3$O)$_3$Si(CH$_2$)$_3$N$^+$(CH$_3$)$_2$(CH$_2$)$_3$NHSO$_2$(CF$_2$)$_9$ CF$_3$,
(CH$_3$O)$_3$Si(CH$_2$)$_3$N$^+$(CH$_3$)$_2$(CH$_2$)$_3$NHSO$_2$(CF$_2$)$_{11}$ CF$_3$,
(CH$_3$O)$_3$Si(CH$_2$)$_3$N$^+$(CH$_3$)$_2$(CH$_2$)$_3$NHSO$_2$(CF$_2$)$_{13}$ CF$_3$,
(CH$_3$O)$_3$Si(CH$_2$)$_3$N$^+$(CH$_3$)$_2$(CH$_2$)$_3$NHSO$_2$(CF$_2$)$_{15}$ CF$_3$,
(CH$_3$O)$_3$Si(CH$_2$)$_3$N$^+$(CH$_3$)$_2$(CH$_2$)$_3$NHSO$_2$(CF$_2$)$_{16}$ CF$_3$,
3-(trimethoxysilyl)propyldimethyloctadecyl ammonium chloride, 3-(trimethoxysilyl)propylmethyldi(decyl) ammonium chloride, 3-chloropropyltrimethylsilane, octadecyltrimethoxysilane, perfluorooctyltriethoxysilane, aminoethylaminopropyltrimethoxysilane, 3-aminopropyltrimethoxysilane, 3-aminopropyltriethoxysilane, 3-chloropropyltrimethoxysilane, 3-chloropropyltriethoxysilane, 3-chloropropyltrichlorosilane, 3-glycidoxypropyltrimethoxysilane, 3-glycidoxypropyltriethoxysilane, 3-methacryloxypropyltrimethoxysilane, 3-methacryloxypropyltriethoxysilane, methyldichlorosilane, sodium(trihydroxysilyl)propylmethylphosphonate, trichlorosilane, n-2-vinylbenzylamino-ethyl-3-aminopropyltrimethoxysilane HCl, vinyltriacetoxysilane, vinyltrimethoxysilane, vinyltriethoxysilane, vinyltrichlorosilane, dimethyldichlorosilane, dimethyldimethoxysilane, diphenyldichlorosilane, ethyltrichlorosilane, ethyltrimethoxysilane, ethyltriethoxysilane, isobutyltrimethoxysilane, n-octyltriethoxysilane, methylphenyldichlorosilane, methyltrichlorosilane, methyltrimethoxysilane, phenyltrichlorosilane, phenyltrimethoxysilane, n-propyltrichlorosilane, n-propyltrimethoxysilane, silicon tetrachloride, ClCH$_2$C$_6$H$_4$CH$_2$CH$_2$SiCl$_3$, ClCH$_2$C$_6$H$_4$CH$_2$CH$_2$Si(OCH$_3$)$_3$, ClCH$_2$C$_6$H$_4$CH$_2$CH$_2$Si(OCH$_2$CH$_3$)$_3$, decyltrichlorosilane, dichloromethyl(4-methylphenethyl)silane, diethoxymethylphenylsilane, [3-(diethylamino)propyl]trimethoxysilane, 3-(dimethoxymethylsilyl)-1-propanethiol, dimethoxymethylvinylsilane, 3-[tris(trimethylsilyloxy)silyl]propyl methacrylate, trichloro[4-(chloromethyl)phenyl]silane, methylbis(trimethylsilyloxy)vinylsilane, methyltripropoxysilane, or trichlorocyclopentylsilane.

21. The composition of claim 19, wherein the organosilane is 3-(trimethoxysilyl)propyldimethyloctadecyl ammonium chloride.

22. The composition of claim 19, wherein the polyol is pentaerythritol, dipentaerythritol, tripentaerythritol, tetrapentaerythritol, tris(hydroxymethyl)ethane, tris(hydroxymethyl)propane, tris(hydroxymethyl)nitromethane, tris(hydroxymethyl)aminomethane, tris(hydroxymethyl)methane trimethyl ammonium iodide, or tetrakis(hydroxymethyl)phosphonium chloride.

23. The composition of claim 19, wherein the polyol is pentaerythritol.

24. The composition of claim 19, wherein (1) the organosilane is 3-(trimethoxysilyl)propyldimethyloctadecyl ammonium chloride, 3-(trimethoxysilyl)propylmethyldi(decyl)ammonium chloride, 3-chloropropyltrimethylsilane, 3-chloropropyltrimethoxysilane, octadecyltrimethoxysilane, or perfluorooctyltriethoxysilane and (2) the polyol is pentaerythritol, dipentaerythritol, tripentaerythritol, tetrapentaerythritol, tris(hydroxymethyl)ethane, tris(hydroxymethyl)propane, tris(hydroxymethyl)nitromethane, tris(hydroxymethyl)aminomethane, or tris(hydroxymethyl)methanetrimethyl ammonium iodide.

25. The composition of claim 19, wherein the organosilane is 3-(trimethoxysilyl)propyldimethyloctadecyl ammonium chloride and the polyol is pentaerythritol.

26. A coating composition comprising the composition of claim 19, wherein the composition is from 0.1 to 1% by volume of the coating composition.

27. The composition of claim 19, wherein the compound is monomeric.

28. The composition of claim 19, wherein the compound is oligomeric.

29. The composition of claim 19, wherein the compounds of the composition are substantially monomeric.

30. The composition of claim 19, wherein the compounds of the composition are substantially oligomeric.

31. The composition of claim 19, wherein the polyol has the structure XX, XXV, or XXX:

 (XX)

 (XXV)

or

 (XXX)

wherein n is an integer of from 0 to 4;

$R_{17}$ is a functional group comprising —COOH, —P(O)(OH)$_2$, —SO$_3$H, —B(OH)$_2$, —P(O)(OH), or —P(O)(OH)(OR$_{18}$), where $R_{18}$ is a branched or unbranched alkyl group or perfluoroalkyl group having from 1 to 22 carbon atoms; an aryl group; a heteroaryl group; or a polyether, wherein any hydrogen of a selected hydroxy group on the functional group can be replaced with Na$^+$, K$^+$, NH$_4^+$, Mg$^{2+}$, Ca$^{2+}$, or N(R$_{70}$)$_4^1$, wherein $R_{70}$ is a branched or unbranched alkyl group or perfluoroalkyl group having from 1 to 22 carbon atoms; an aryl group; a heteroaryl group; or a polyether.

32. The composition of claim 19, wherein the polyol has the structure XXXV or XL:

 (XXXV)

or

 (XL)

wherein $R_{14}$ and $R_{15}$ are, independently, hydrogen; an alkyl group having from 1 to 4 carbon atoms that is unsubstituted or substituted with a hydroxy group; a polyalkylether group; or a benzyl group;

$R_{16}$ is hydrogen, a phenyl group; an alkyl group having from 1 to 22 carbon atoms that is unsubstituted or substituted with a hydroxy group; or a polyalkylether group, and U is a halogen, a sulfate, a tosylate, a carboxylate, an alkylsulfonate, an arylsulfonate, a phosphate, a phosphonate salt, a borate, or a boronate salt.

33. A water-stable composition comprising water and a compound having the formula (R)$_n$Si(X)$_{4-y-n}$(R$_{41}$)$_y$, wherein n is an integer of from 0 to 3; y is an integer of from 1 to 4; each R is, independently, a nonhydrolizable organic group; each X is, independently, a hydrolyzable group; and each $R_{41}$ is, independently, a poly(tetrahydrofuran), a poly(vinyl) alcohol, or starch containing at least three hydroxy groups, wherein all of the hydroxy groups are separated by at least three intervening atoms and wherein the $R_{41}$ bonded to the Si by removal of the hydrogen from one of the at least three hydroxy groups such that the oxygen of the one of the at least three hydroxy groups is bonded to Si.

34. A water-stable composition comprising water and a product that is formed by reacting in water an organosilane of the formula II, III, IV, or V:

 (II)

 (III)

 (IV)

 (V)

wherein each $R_1$ of the three is, independently, halogen or R$_6$O, where $R_6$ is H, alkyl of from 1 to about 6 carbon atoms, acetyl, acetoxy or acyl;

$R_{35}$ is H, halogen, NH$_2$(CH$_2$)$_2$NHR$_2$, NH$_2$R$_2$C$_3$H$_5$O$_2$R$_2$, C$_4$H$_5$O$_2$R$_2$, NaO(CH$_3$O)P(O)R$_2$, or ClCH$_2$C$_6$H$_4$R$_2$;

$R_{36}$ and $R_{37}$ are, independently, halogen, H, alkyl of from 1 to about 8 carbon atoms, isobutyl, phenyl, or n-octyl;

$R_2$ is benzyl, vinyl or alkyl of from 1 to about 3 carbon atoms;

$R_3$ and $R_4$ are, independently, lower alkyl alcohol, lower alkoxy of from 1 to 4 carbon atoms, alkyl of from 1 to about 22 carbon atoms; or $R_3$ and $R_4$ can, together, form a morpholine or cyclic or heterocyclic, unsaturated or saturated, five to seven-membered ring of the formula VI:

 (VI)

where k is an integer from 0 to 2, $R_7$, where the ring is saturated, is CH$_2$, O, S, NH, NH$_2^+$, NCH$_2$CH$_2$NH$_2$, NCH$_2$CH$_2$NH$_3^+$, NCH$_2$CH$_2$N(R$_8$)(R$_9$), NCH$_2$CH$_2$N$^+$(R$_8$)(R$_9$)(R$_{10}$), N(alkyl), N(aryl), N(benzyl), where each $R_8$, $R_9$, and $R_{10}$ is, independently, benzyl, polyether, lower alkyl alcohol of from 1 to 4 carbon atoms, lower alkoxy of from 1 to 4 carbon atoms, or alkyl of from 1 to about 22 carbon atoms, and $R_7$, where the ring is unsaturated is, CH, N, N$^+$H, N$^+$(alkyl), N$^+$(aryl), N$^+$(benzyl), N—CH$_2$—N, N$^+$H—CH$_2$—N, N$^+$(alkyl)—CH$_2$—N, N$^+$(aryl)—CH$_2$—N, or N$^+$(benzyl)—CH$_2$—N;

wherein the ring is unsubstituted or substituted with alkyl of from 1 to 22 carbon atoms, ester, aldehyde, carboxylate, amide, thioamide, nitro, amine, or halide $R_5$ is lower alkyl alcohol, $CH_2C_6H_5$, polyether, alkyl, alkoxy, perfluoroalkyl, perfluoroalkylsulfonate, or perfluoroalkylcarboxylate wherein the alkyl, alkoxy, perfluoroalkyl, perfluoroalkylsulfonate, or perfluoroalkylcarboxylate is of from 1 to about 22 carbon atoms; and Y is a suitable anionic moiety to form the salt of the compound of formula II, III, IV or V;

with a poly(tetrahydrofuran), a poly(vinyl)alcohol, starch, or a mixture thereof.

35. A water stable composition consisting essentially of water and a compound that is formed by reacting in water components comprising
a) an organosilane of the formula $R_nSiX_{4-n}$ where n is an integer of from 0 to 3; each R is, independently, a nonhydrolizable organic group; and each X is, independently, a hydrolyzable group, with
b) a polyol containing at least three hydroxy groups, wherein all of the hydroxy groups are separated by at least three intervening atoms, wherein the polyol is not hydroxyethyl cellulose.

36. A water-stable composition comprising water and a product that is formed by reacting in water a) an organosilane of the formula $R_nSiX_{4-n}$ where n is an integer of from 0 to 3; each R is, independently, a nonhydrolizable organic group; and each X is, independently, a hydrolyzable group, with b) a polyol containing at least three hydroxy groups, wherein all of the hydroxy groups are separated by at least three intervening atoms, wherein the organosilane is 3-(trimethoxysilyl)propyldimethyloctadecyl ammonium chloride and the polyol is pentaerythritol.

37. A water-stable composition comprising water and a product that is formed by reacting in water a) an organosilane of the formula $R_nSiX_{4-n}$ where n is an integer of from 0 to 3; each R is, independently, a nonhydrolizable organic group; and each X is, independenely, a hydrolyzable group, with b) a polyol containing at least three hydroxy groups, wherein all of the hydroxy groups are separated by at least three intervening atoms, wherein the organosilane is of the formula II, III, IV, or V:

$$(R_1)_3SiR_2N^+(R_3)(R_4)(R_5)Y^- \qquad (II)$$

$$(R_1)_3SiR_2N(R_3)(R_4) \qquad (III)$$

$$(R_1)_3SiR_2R_{35} \qquad (IV)$$

$$(R_1)_2Si(R_{36})(R_{37}) \qquad (V)$$

wherein each $R_1$ of the three is, independently, halogen or $R_6O$, where $R_6$ is H, alkyl of from 1 to about 6 carbon atoms, acetyl, acetoxy, or acyl;

$R_{35}$ is H, halogen, $NH_2(CH_2)_2NHR_2$, $NH_2R_2C_3H_5O_2R_2$, $C_4H_5O_2R_2$, $NaO(CH_3O)P(O)R_2$, or $ClCH_2C_6H_4R_2$;

$R_{36}$ and $R_{37}$ are, independently, halogen, H, alkyl of from 1 to about 8 carbon atoms, isobutyl, phenyl, or n-octyl;

$R_2$ is benzyl, vinyl or alkyl of from 1 to about 3 carbon atoms;

$R_3$ and $R_4$ are, independently, lower alkyl alcohol, lower alkoxy of from 1 to 4 carbon atoms, alkyl of from 1 to about 22 carbon atoms; or $R_3$ and $R_4$ can, together, form a morpholine or cyclic or heterocyclic, unsaturated or saturated, five to seven-membered ring of the formula VI:

$$-R_3-(R_7)_k-R_4- \qquad (VI)$$

where k is an integer from 0 to 2, $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), where each $R_8$, $R_9$, and $R_{10}$ is, independently, benzyl, polyether, lower alkyl alcohol of from 1 to 4 carbon atoms, lower alkoxy of from 1 to 4 carbon atoms, or alkyl of from 1 to about 22 carbon atoms, and $R_7$, where the ring is unsaturated is, CH, N, $N^+H$, $N^+(alkyl)$, $N^+(aryl)$, $N^+(benzyl)$, $N-CH_2-N$, $N^+H-CH_2-N$, $N^+(alkyl)-CH_2-N$, $N^+(aryl)-CH_2-N$, or $N^+(benzyl)-CH_2-N$;

wherein the ring is unsubstituted or substituted with alkyl of from 1 to 22 carbon atoms, ester, aldehyde, carboxylate, amide, thioamide, nitro, amine, or halide $R_5$ is lower alkyl alcohol, $CH_2C_6H_5$, polyether, alkyl, alkoxy, perfluoroalkyl, perfluoroalkylsulfonate, or perfluoroalkylcarboxylate wherein the alkyl, alkoxy, perfluoroalkyl, perfluoroalkylsulfonate, or perfluoroalkylcarboxylate is of from 1 to about 22 carbon atoms; and $Y^-$ is a suitable anionic moiety to form the salt of the compound of formula II, III, IV or V;

and where the polyol is of the formula I:

$$\{R_{11}(W)_p\}(R_{33})_{3-o}C\{(CH_2)_qOH\}_o \qquad (I)$$

wherein o is an integer of from 2 to 3;

q is an integer of from 1 to 2, p is an integer of from 0 to 1;

W is alkyl, polyether, aryl or heteroaryl;

$R_{11}$ and $R_{33}$ are, independently, halogen, H, $CH_2OH$, $N(CH_2CH_2OH)_2CH_3^+V^-$, $NH_2$, $NO_2$, $N(H)(CH_2)_3OSO_3H$, $N^+(CH_3)_2(CH_2)_3SO_3^-$, $N(CH_3)_3^+V^-$, $(CH_2)OPO_3H_2$, $(CH_2)PO_3H_2$, $N(H)R_{34}(CF_2)_eCF_3$ where e is an integer of from 1 to about 22 and $R_{34}$ is CO or $SO_2$, $N(H)R_{34}(CF_2)_eCF_3$ where e is an integer of from 1 to about 22 and $R_{34}$ is CO or $SO_2$, $(W)_pZO$ where Z is H, alkyl, aryl, or heteroaryl, $(W)_pZS(O)_r$ where Z is H, Na, a suitable mono- or di-valent cation, alkyl, aryl, or heteroaryl and r is an integer from 0 to 2, $(W)_pZ_1Z_2N$ where $Z_1$ and $Z_2$ are, independently, H, alkyl, aryl, or heteroaryl, $(W)_pZ_3Z_4Z_5N^+Q^-$ where $Z_3$, $Z_4$, and $Z_5$ are, independently, H, alkyl, aryl, or heteroaryl and where $Q^-$ is a suitable anionic moiety to form a salt, or $(W)_pZ_6PO_3$ where $Z_6$ is H, Na, a suitable mono- or di-valent cation, alkyl, aryl, or heteroaryl; and $V^-$ is a suitable anionic moiety to form the salt of the compound of formula I.

38. The composition of claim 37 wherein each of Y and V is, independently, halide, sulfate, tosylate, carboxylate, polycarboxylate, alkyl, arylsulfonate, phosphate, phosphonate, borate, or boronate.

39. A water-stable composition comprising water and a product that is formed by reacting in water a) an organosilane of the formula $R_nSiX_{4-n}$ where n is an integer of from 0 to 3; each R is, independently, a nonhydrolizable organic group; and each X is, independently, a hydrolyzable group, with b) a polyol containing at least three hydroxy groups, wherein all of the hydroxy groups are separated by at least three intervening atoms, wherein the polyol is a compound having the formula VII:

$(R_{12})(R_{13})C\{(CH_2)_sR_{14}\}_2$ (VII)

wherein s is an integer of from 1 to 2, $R_{12}$ is $(CH_2)_gR_{14}$ where g is an integer of from 0 to 10, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$; $N^+(CH_3)_3T^-$, $N^+(R_{17})(R_{18})(R_{19})T^-$, where $R_{15}$, $R_{16}$, $R_{17}$, and $R_{18}$ are, independently, H, O, or lower alkyl of from 1 to about 4 carbon atoms, polyalkyl ester, benzyl, or $R_{15}$ and $R_{16}$, together, or $R_{17}$ and $R_{18}$, together, may, independently, form an amide, sulfonamide, phosphonamide, oxime, thioamide, quaternary ammonium, imine, imide, guanidine, piperazine, morpholine, or $N(O)R_{20}R_{21}$, where $R_{20}$ and $R_{21}$ are, independently, lower alkyl alcohol of from 1 to 4 carbon atoms, lower alkoxy of from 1 to 4 carbon atoms, or alkyl of from 1 to about 4 carbon atoms;

$R_{19}$ is H or alkyl of from 1 to about 22 carbon atoms; and $T^-$ is a suitable anionic moiety to form a quaternary ammonium salt of the compound of formula VII;

$R_{13}$ is H, OH, $(CH_2)_5R_{14}$, $(CH_2)OPO_3H_2$, or $(CH_2)PO_3H_2$, lower alkyl of from 1 to 4 carbon atoms, lower alkoxy of from 1 to about 4 carbon atoms; and each $R_{14}$ is, independently, OH or $\{-CH_2C(CH_2OH)_2CH_2O\}_j-H$ where j is an integer of from 0 to 5 and wherein one of the $R_{14}$ moieties is bonded to the Si by removal of the hydrogen from a hydroxy such that the oxygen of the hydroxy is bonded to Si;

or a perfluoro-analog thereof; or a mixture thereof.

40. The composition of claim 39, wherein g is an integer of from 0 to 3; $R_{12}$ is $(CH_2)_gR_{14}$, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(CH_3)_3T^-$, or $N^+(R_{17})(R_{18})(R_{19})T^-$;

$R_{13}$ is H, OH, $(CH_2)_sR_{14}$, $(CH_2)OPO_3H_2$, or $(CH_2)PO_3H_2$, lower alkyl of from 1 to 4 carbon atoms, lower alkoxy of from 1 to about 4 carbon atoms, and each $R_{14}$ is, independently, OH or $\{-CH_2C(CH_2OH)_2CH_2O\}_j-H$ where j is an integer of from 0 to 5.

41. The composition of claim 39, wherein $R_{12}$ is $(CH_2)_gR_{14}$, lower alkyl of from 1 to about 4 carbon atoms, or lower alkoxy of from 1 to about 4 atoms.

42. The composition of claim 39, wherein $R_{12}$ is $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(CH_3)_3T^-$, or $N^+(R_{17})(R_{18})(R_{19})T^-$.

43. The composition of claim 39, wherein g is an integer of from 0 to 3; $R_{12}$ is $(CH_2)_gR_{14}$, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(CH_3)_3T^-$, or $N^+(R_{17})(R_{18})(R_{19})T^-$; and each $R_{14}$ is OH.

44. The composition of claim 39, wherein g is an integer of from 0 to 3; $R_{12}$ is $(CH_2)_gR_{14}$, lower alkyl of from 1 to about 4 carbon atoms, lower alkoxy of from 1 to about 4 carbon atoms, $N(R_{15})(R_{16})$, $N(H)(CH_2)_3OSO_3H$, $N(H)(CH_2)_3OSO_3H$, $N(H)(CH_2)_3OSO_3H$, $N^+(CH_3)_2(CH_2)_3SO_3^-$, $N^+(CH_3)_3T^-$, or $N^+(R_{17})(R_{18})(R_{19})T^-$; and each $R_{14}$ is, independently, $\{-CH_2C(CH_2OH)_2CH_2O\}_j-H$ where j is an integer of from 0 to 5 and wherein one of the $R_{14}$ moieties is bonded to the Si by removal of the hydrogen from a hydroxy such that the oxygen of the hydroxy is bonded to Si.

* * * * *